(12) United States Patent
Del Bon

(10) Patent No.: US 7,234,459 B2
(45) Date of Patent: Jun. 26, 2007

(54) NEBULISER DEVICE FOR AN INHALER APPARATUS AND INHALER APPARATUS WITH SUCH NEBULISER DEVICE

(76) Inventor: Franco Del Bon, Eggenacherstrasse 52, CH 4663, Aarburg (CH)

(*) Notice: Subject to any disclaimer, the term of this patent is extended or adjusted under 35 U.S.C. 154(b) by 585 days.

(21) Appl. No.: 10/384,734

(22) Filed: Mar. 11, 2003

(65) Prior Publication Data

US 2004/0177849 A1    Sep. 16, 2004

(51) Int. Cl.
*A61M 11/00* (2006.01)
(52) U.S. Cl. ............... 128/200.21; 128/200.18; 128/200.14; 239/338
(58) Field of Classification Search .......... 128/200.14, 128/200.21, 200.23, 203.12, 203.14, 203.15
See application file for complete search history.

(56) References Cited

U.S. PATENT DOCUMENTS

| | | | | |
|---|---|---|---|---|
| 3,362,405 A | * | 1/1968 | Hamilton | 128/203.15 |
| 3,931,554 A | * | 1/1976 | Spentzas | 318/122 |
| 4,429,835 A | * | 2/1984 | Brugger et al. | 239/338 |
| 4,739,754 A | * | 4/1988 | Shaner | 128/203.15 |
| 4,907,583 A | * | 3/1990 | Wetterlin et al. | 128/203.15 |
| 5,054,477 A | * | 10/1991 | Terada et al. | 128/200.14 |
| 5,309,900 A | * | 5/1994 | Knoch et al. | 128/200.14 |
| 6,397,838 B1 | * | 6/2002 | Zimlich et al. | 128/200.14 |

FOREIGN PATENT DOCUMENTS

| | | |
|---|---|---|
| GB | 201003 | 7/1923 |
| GB | 471127 | 8/1937 |
| JP | 57184424 | 11/1982 |

* cited by examiner

*Primary Examiner*—Anhtuan T. Nguyen
*Assistant Examiner*—Darwin P. Erezo
(74) *Attorney, Agent, or Firm*—Buchanan Ingersoll & Rooney PC

(57) ABSTRACT

An inhaler device having a pump unit (P) for producing a stream of compressed air, a drive (G) for the pump unit and a nebuliser unit (Z) which communicates with the pump unit and which is driven pneumatically. The inhaler device produces and releases an air stream which is charged in controlled manner with fine liquid active ingredient particles. The pump unit (P) is equipped with a short-stroke piston pump. The drive takes the form of a crank gear (G) having a gear transmission which can be driven by means of a hand crank (K), the output shaft of which is kinematically connected to the pump piston via an eccentric and drives the pump piston. The inhaler device need not use any elaborate energy supply and can be built in compact and handy fashion. It can be ready for use anytime and anywhere and is therefore particularly suitable for mobile use.

12 Claims, 16 Drawing Sheets

Figure 1:
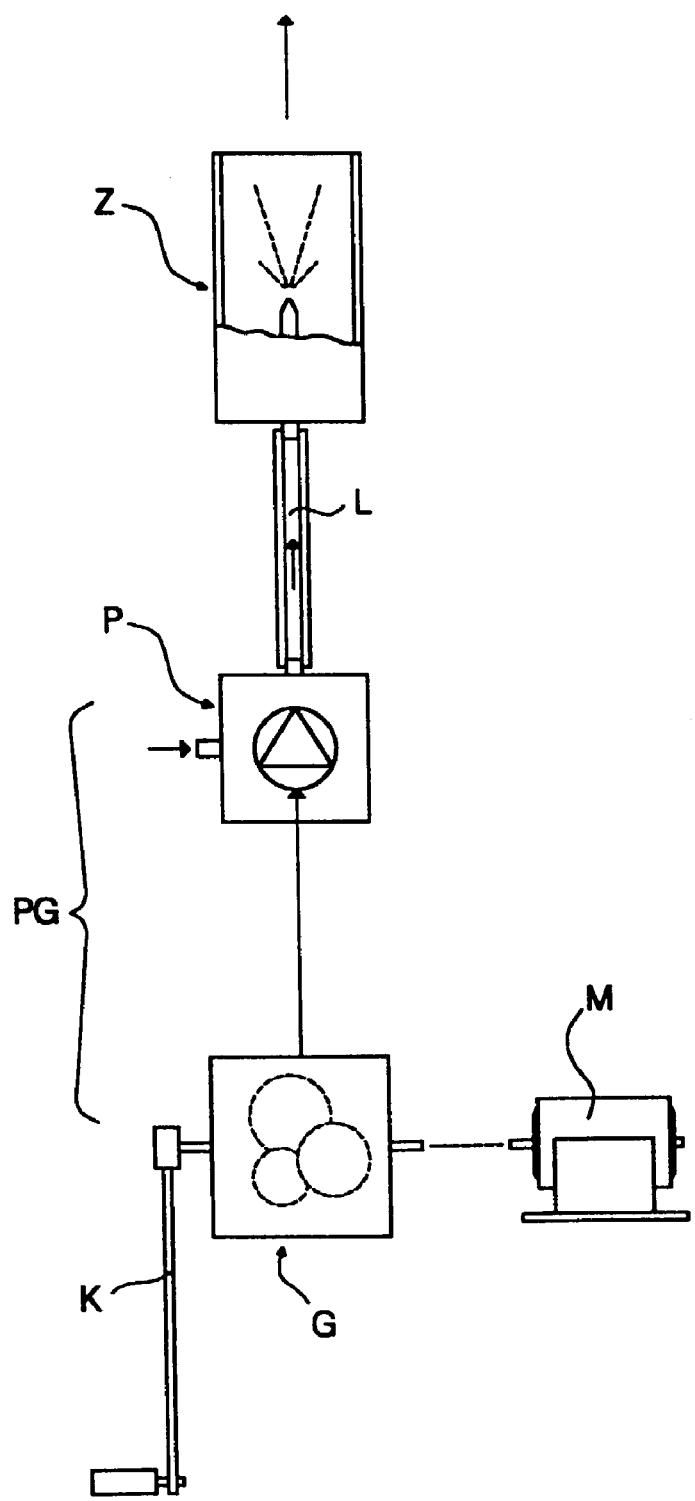

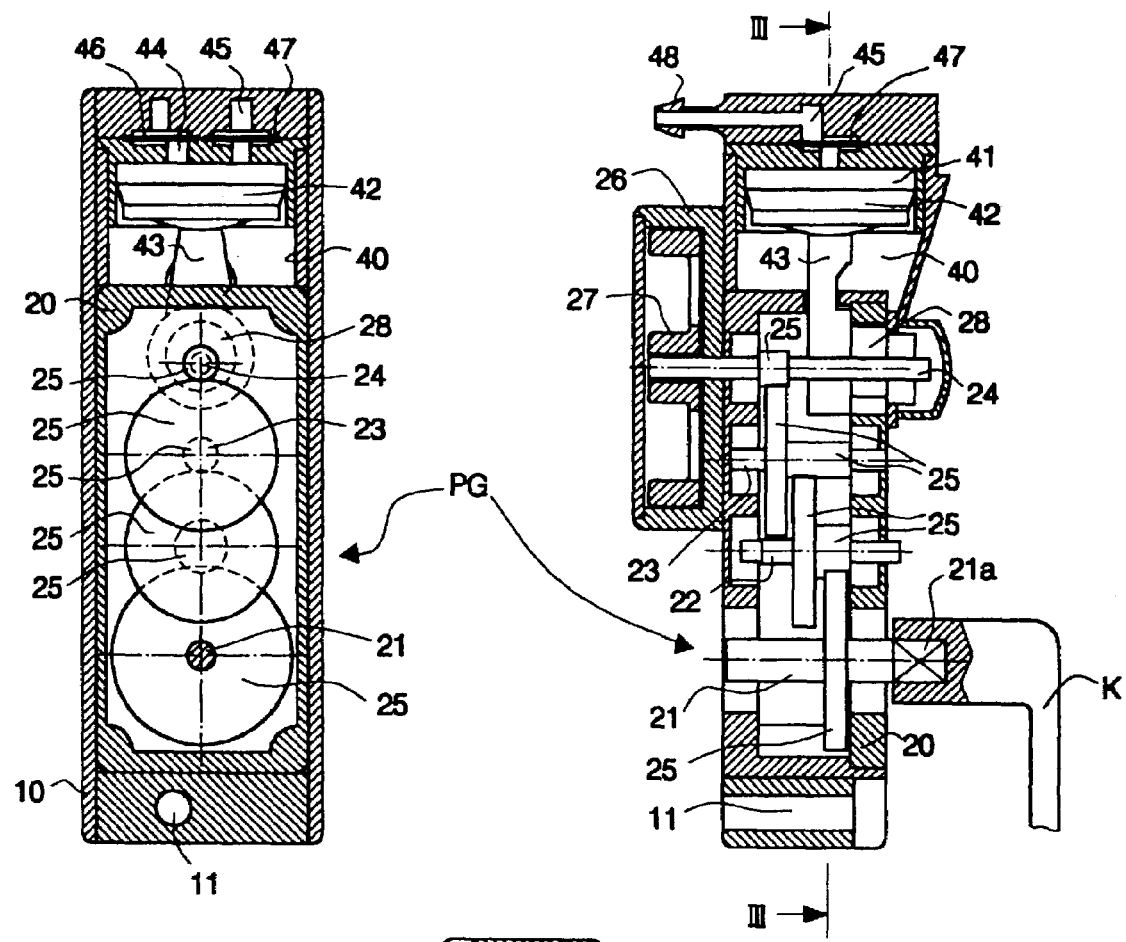
Fig. 3
Fig. 2
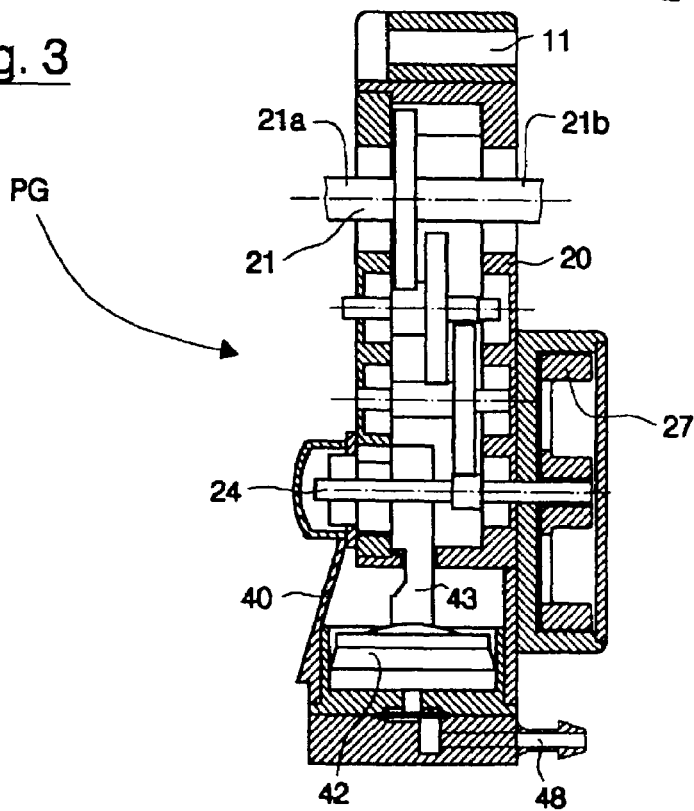
Fig. 4

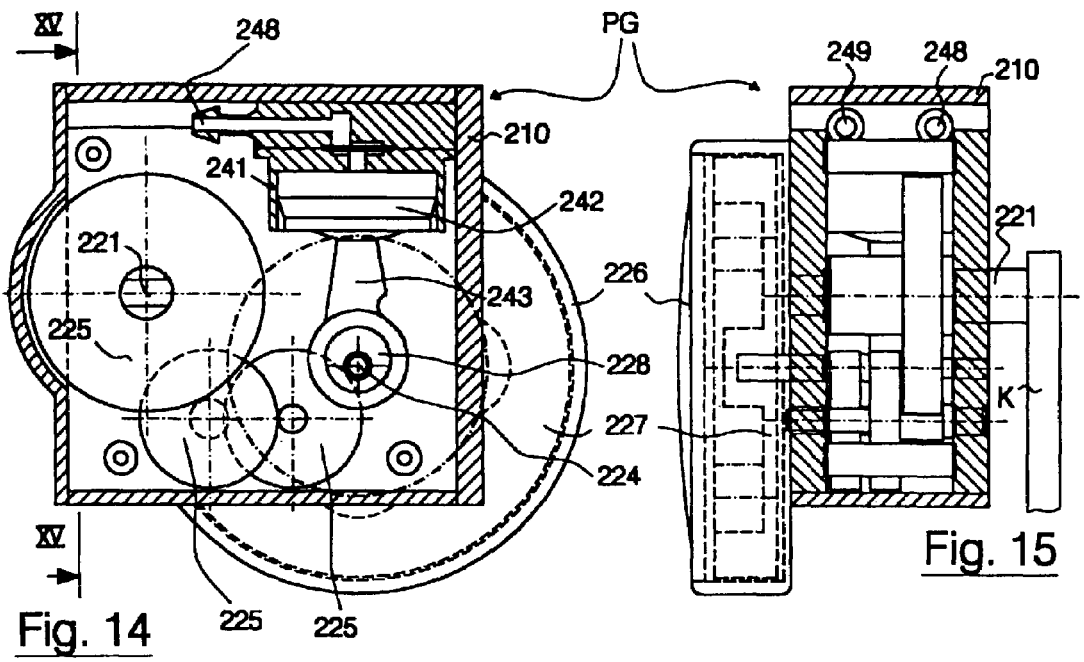
Fig. 14
Fig. 15
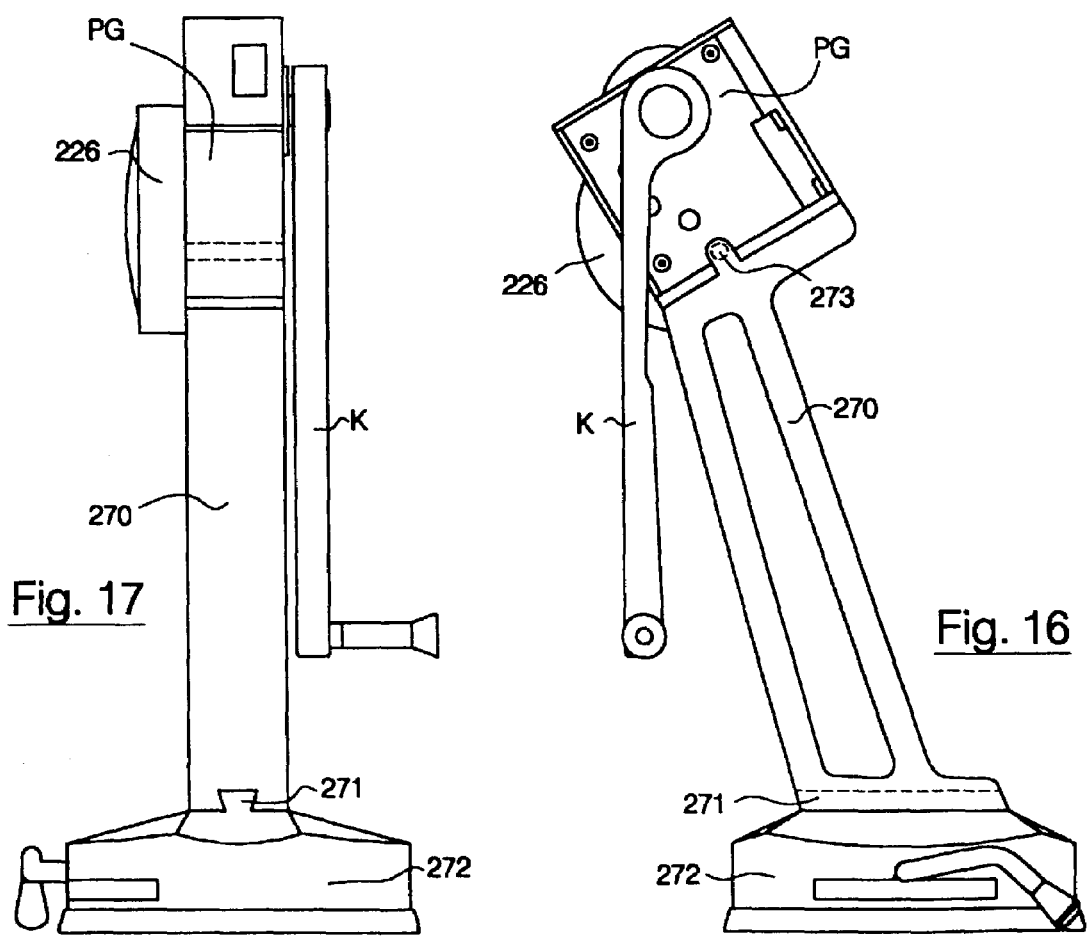
Fig. 17
Fig. 16

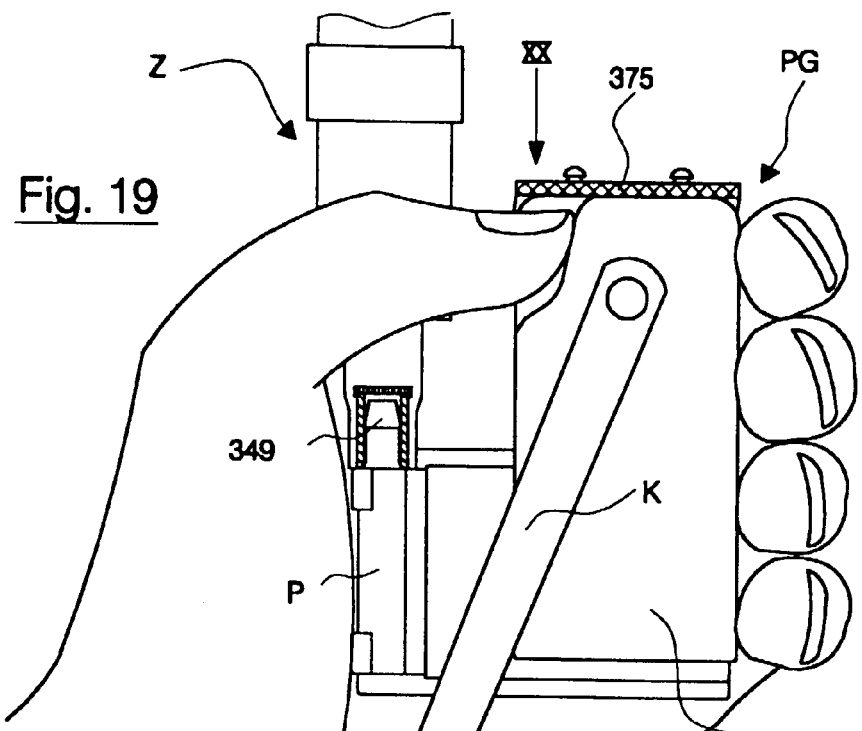
Fig. 19
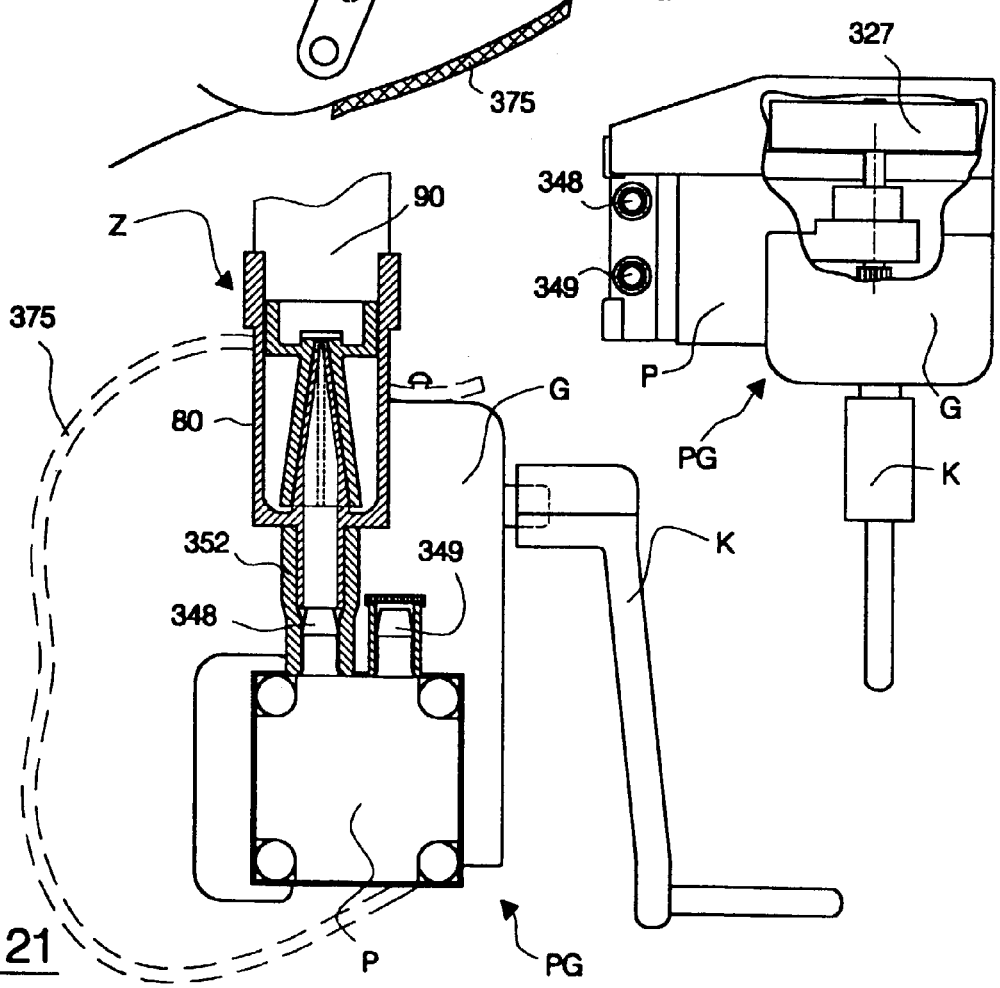
Fig. 20
Fig. 21

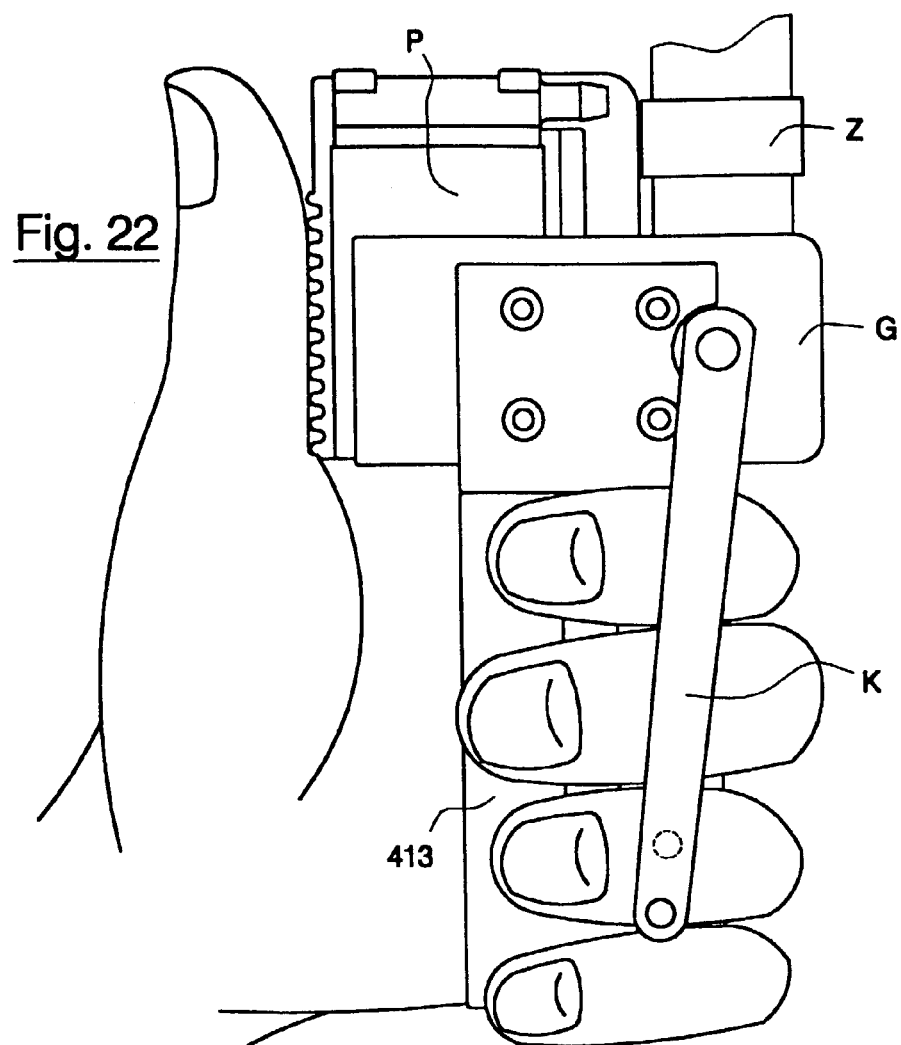
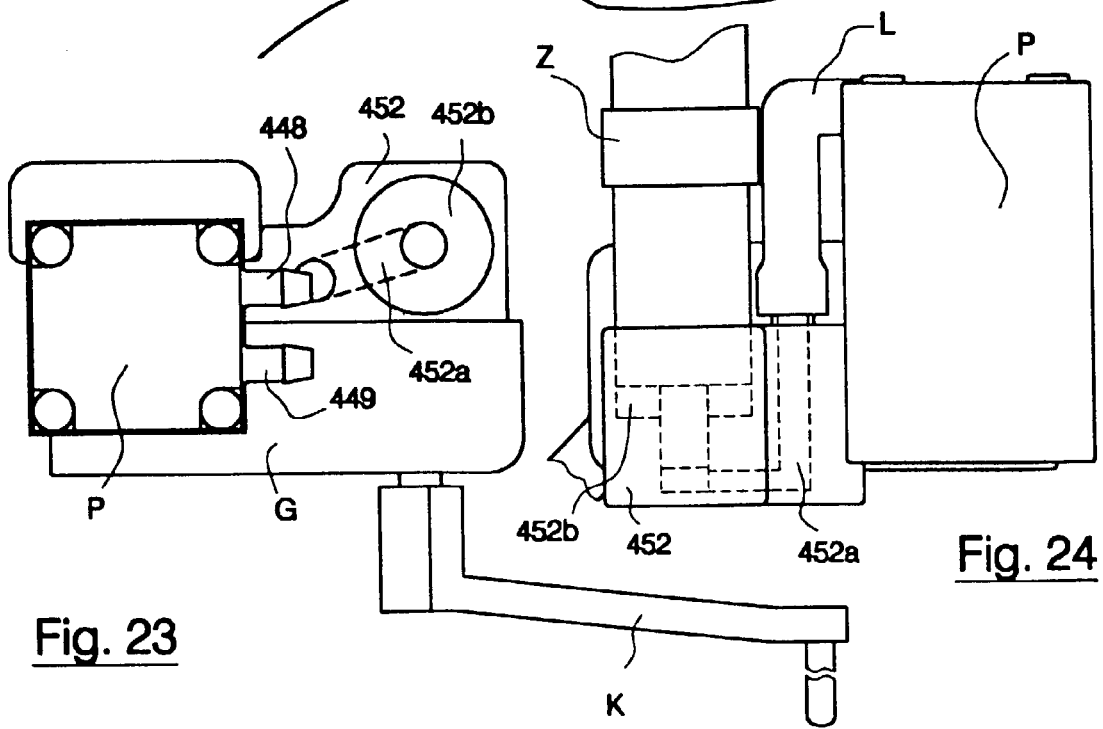

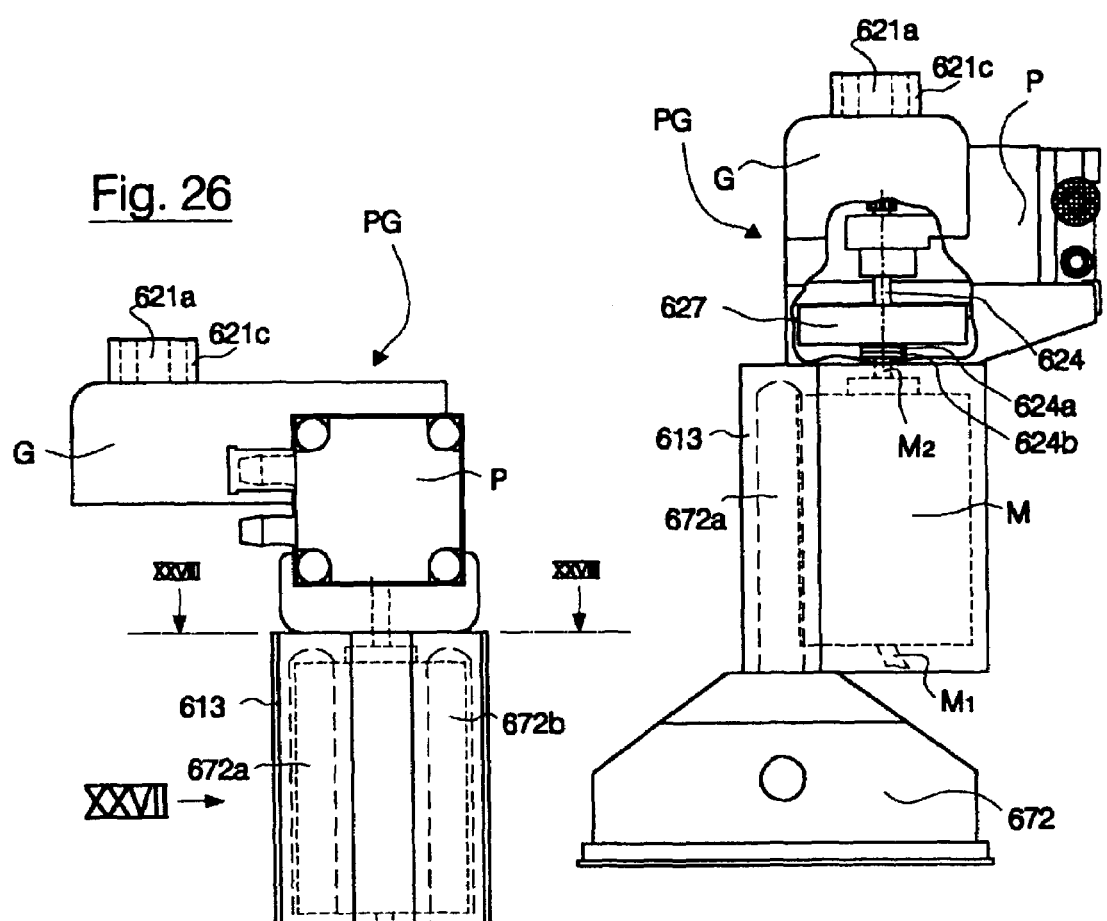
Fig. 26
Fig. 27
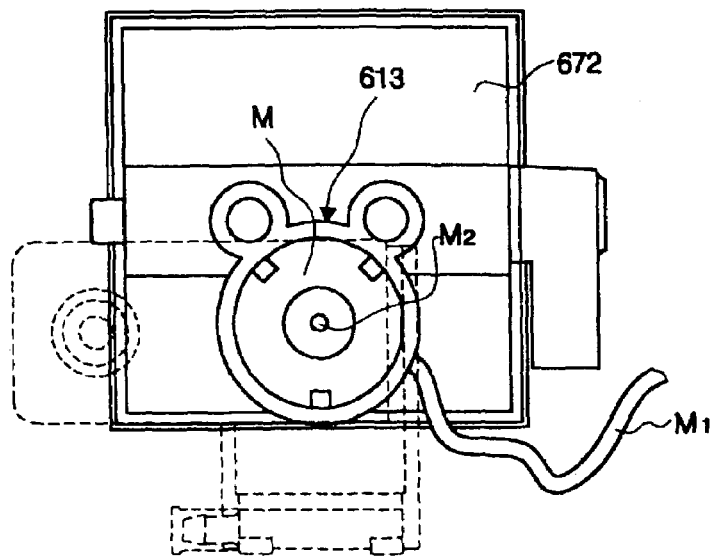
Fig. 28

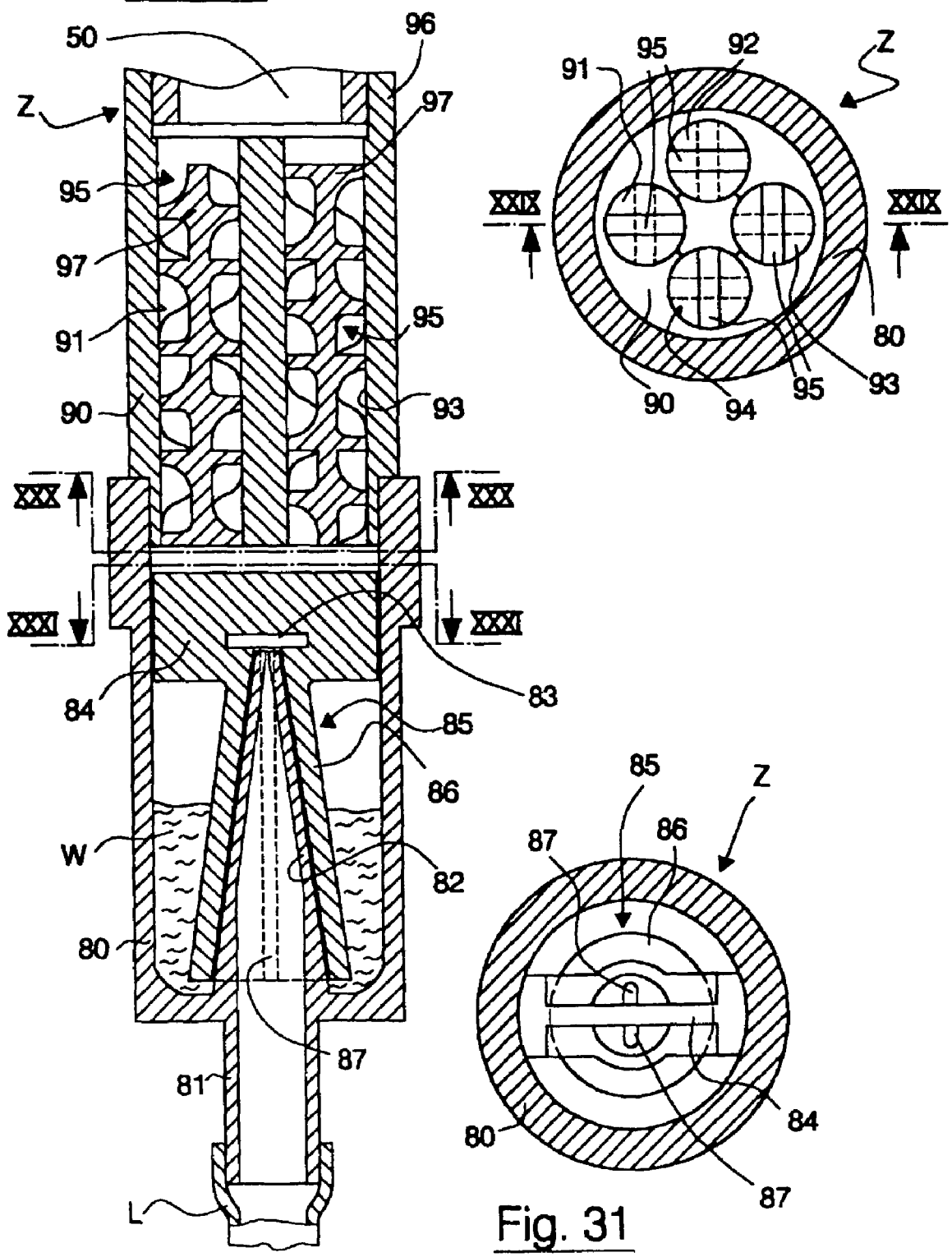

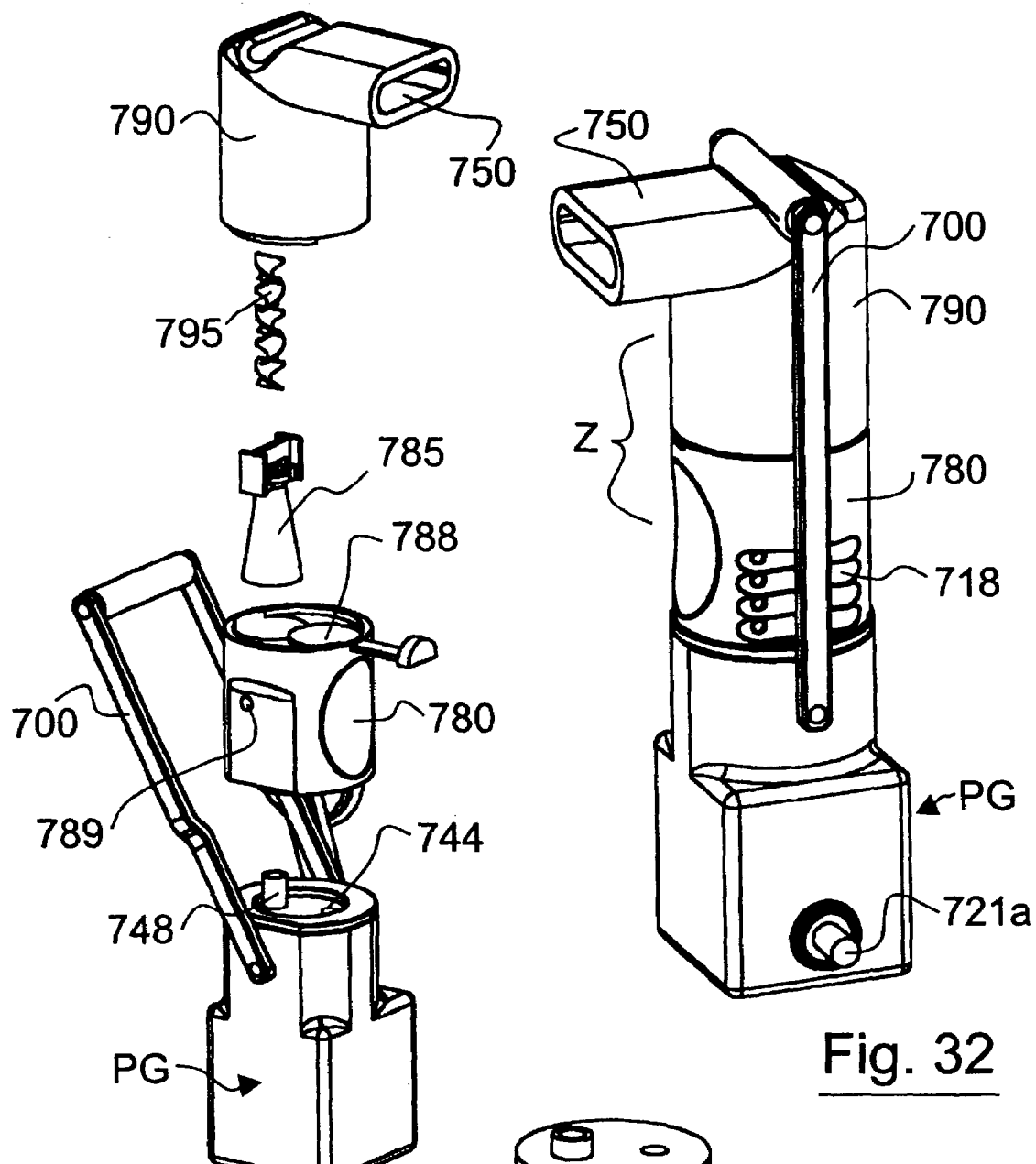
Fig. 32
Fig. 33
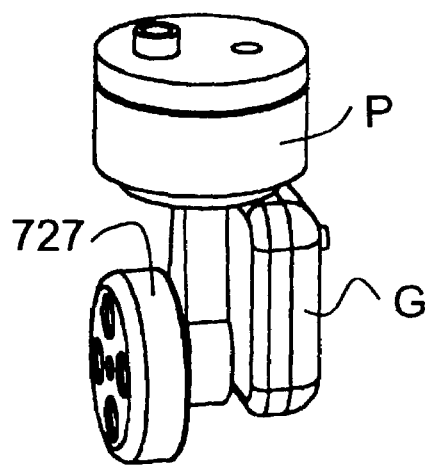

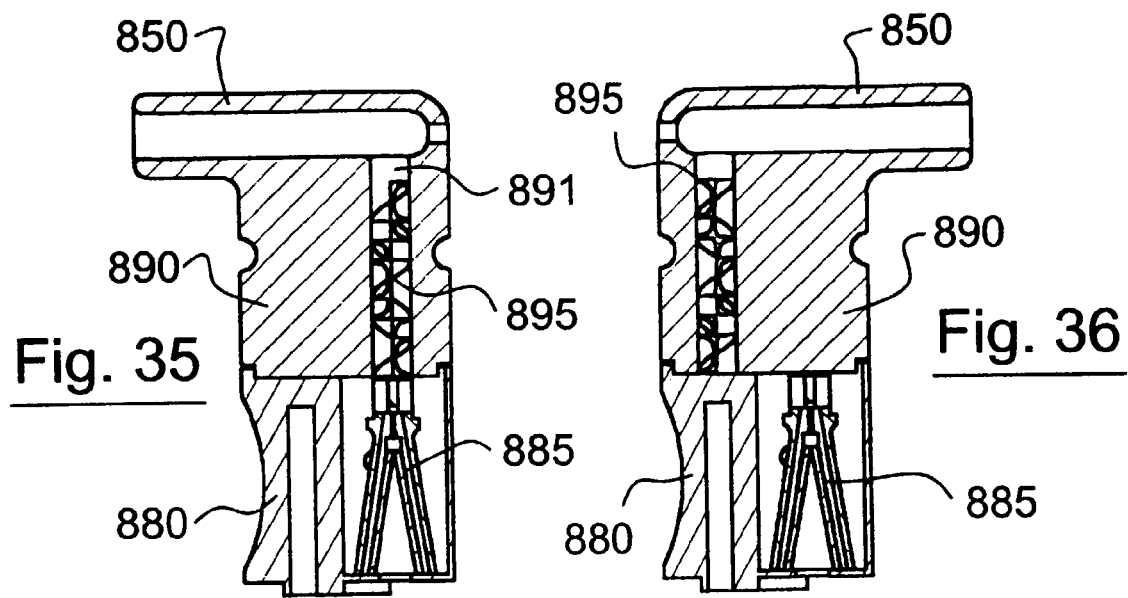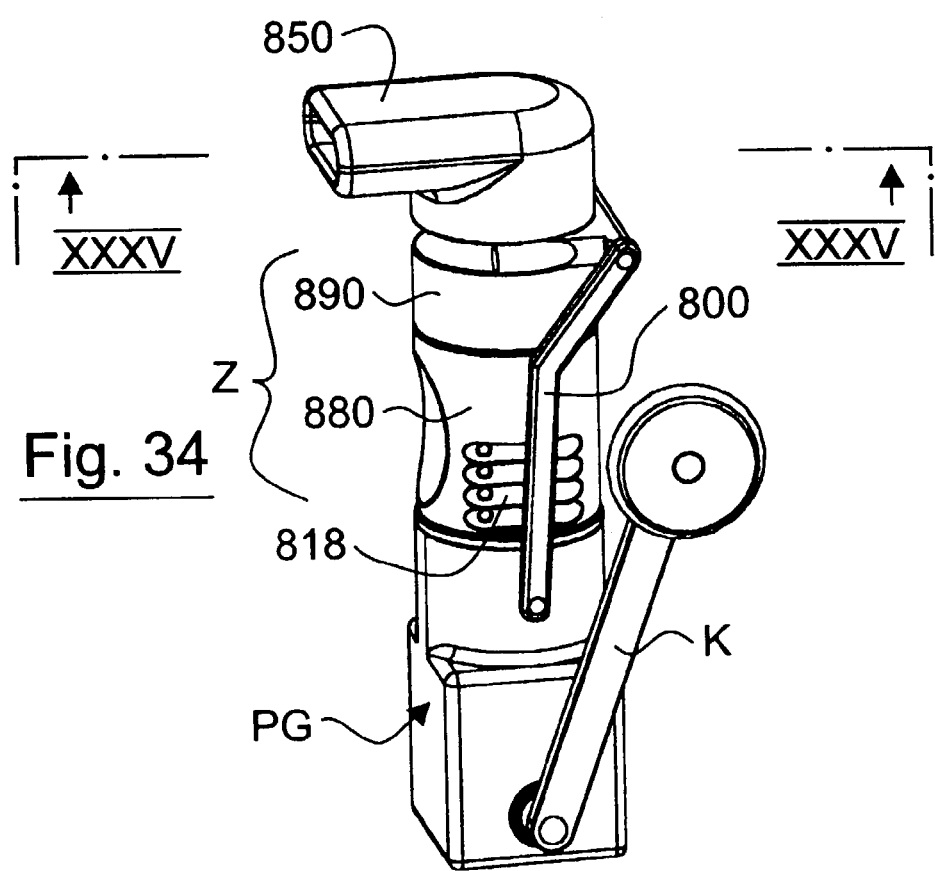

NEBULISER DEVICE FOR AN INHALER APPARATUS AND INHALER APPARATUS WITH SUCH NEBULISER DEVICE

RELATED APPLICATIONS

This application claims priority under 35 U.S.C. §119 to Swiss Application 1828/00 filed in Switzerland on 20 Sep. 2000 and to Swiss Application 0849/01 filed in Switzerland on 10 May 2001, and under 35 U.S.C. §120 to PCT/CH01/00515 filed as an International Application on 23 Aug. 2001, the entire contents of which are hereby incorporated by reference.

BACKGROUND

The present invention relates to a nebuliser device intended for an inhaler. The invention also relates to an inhaler apparatus equipped with such a nebuliser device.

Bronchial therapy normally uses inhaler apparatuses which permit the fine dispersion of a liquid or powdered active ingredient formulation and its controlled release into an air stream which is inhaled by the patient. To achieve optimum efficacy it is important that as large as possible a part of the particles (droplets) produced in this manner has a maximum size of $5\mu$.

Classic inhaler apparatuses more or less meeting these requirements use pneumatic nebulisers equipped with electrically powered compressors. Owing to the required compressors, power units or accumulators, these apparatuses are comparatively voluminous and heavy and are therefore only of limited suitability for mobile use.

Although inhaler apparatuses equipped with nebulisers based on ultra-sound are in general lighter and less voluminous, they are substantially less efficient. Tests have shown that only about 35% of the particles produced with such apparatuses have the required size of less than $5\mu$. Moreover, like the apparatuses equipped with pneumatic nebulisers they require electric energy and their mobile use is therefore relatively complicated, at least when used together with the components required for the electricity supply. The ultrasonic influence may furthermore also destroy the medicinal drug.

A nebuliser device of the generic type is known from document EP-A-0608176. This document discloses a pneumatically driven nebuliser device especially designed and meant for air purification applications, which device produces and releases into the ambient air a fine haze of active ingredient formulation by means of a fractionating cascade in-line with a nebuliser nozzle. The device is conceived for stationary use and is meant for continuous operation at an air through-put of 150–200 litres per hour. A relatively large amount of liquid active ingredient formulation gets caught in the fractioning cascade and has to flow back, which requires an essentially vertical operating position of the nebuliser. For the intermittent operation of a portable inhaler apparatus which in practice often lasts only for a few breaths, the nebuliser device designed for stationary continuous operation is at best of limited suitability also because of the limitation of the operating position.

SUMMARY

The present invention shall now improve a nebuliser device of the generic type such that it meets the special conditions of a portable, in particular manually driven inhaler apparatus and that it can be used in such a device while at the same time having a sufficiently high efficacy for the use in an inhaler apparatus (measured by the proportion of particles having a size equal to or smaller than $5\mu$). In particular, the nebuliser device must be able to operate essentially independently from the operating position and it must be suitable for the intermittent operation with extremely uneven flow conditions.

According to this invention, a desired improvement is achieved through a special design of the mixing means in-line with the nebuliser nozzle. Concretely, this special design involves the mixing body in the mixing means comprising several consecutive mixing elements in the form of helicoids rotating in opposite directions.

Document JP-A-57184424 discloses a dispersing medium (mixer) for dispersing drops of a first fluid in a second, different fluid. This mixer comprises two cascades of 6 helicoid elements each which are arranged in pairs rotationally staggered through 90°. The two cascades are located in a tube having a square cross-section and are arranged at a mutual distance corresponding to the length of the cascade. The dispersing medium known from that document is on the one hand not a nebuliser device and on the other hand is not meant for use in an inhaler apparatus.

BRIEF DESCRIPTION OF THE PREFERRED EMBODIMENTS

Figure 7:
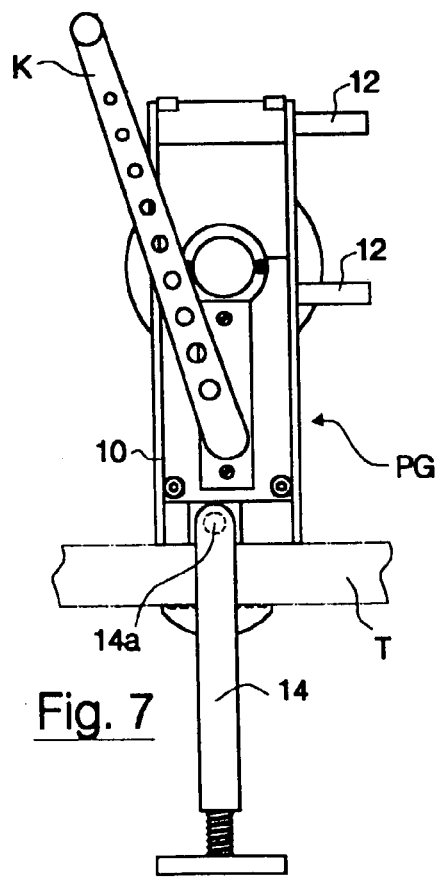
Figure 8:
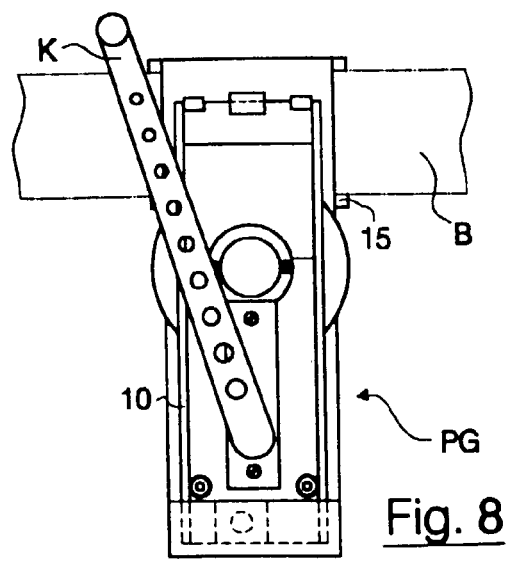
Figure 9:
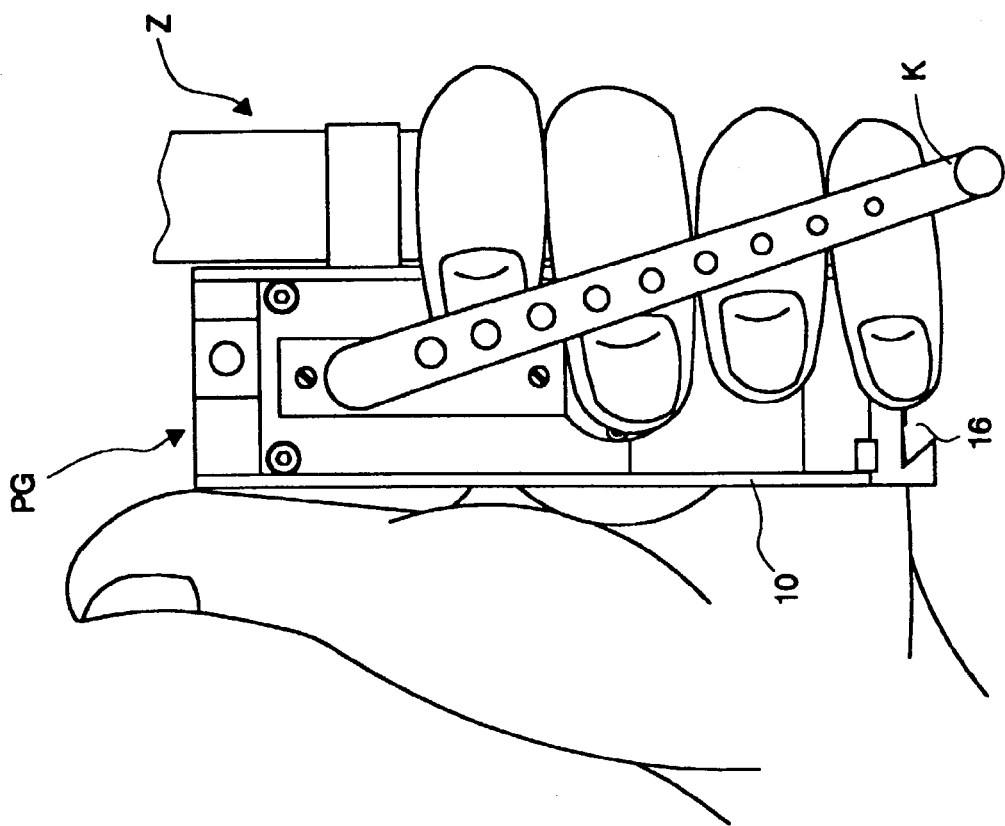
Figure 25:
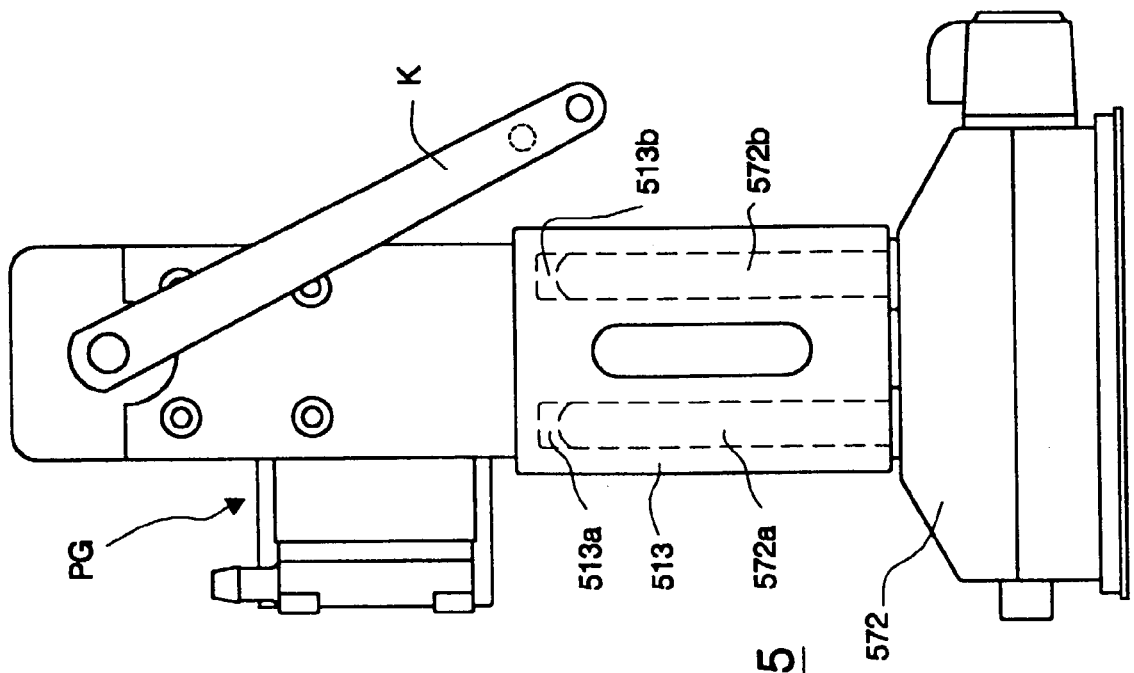
Figure 10:
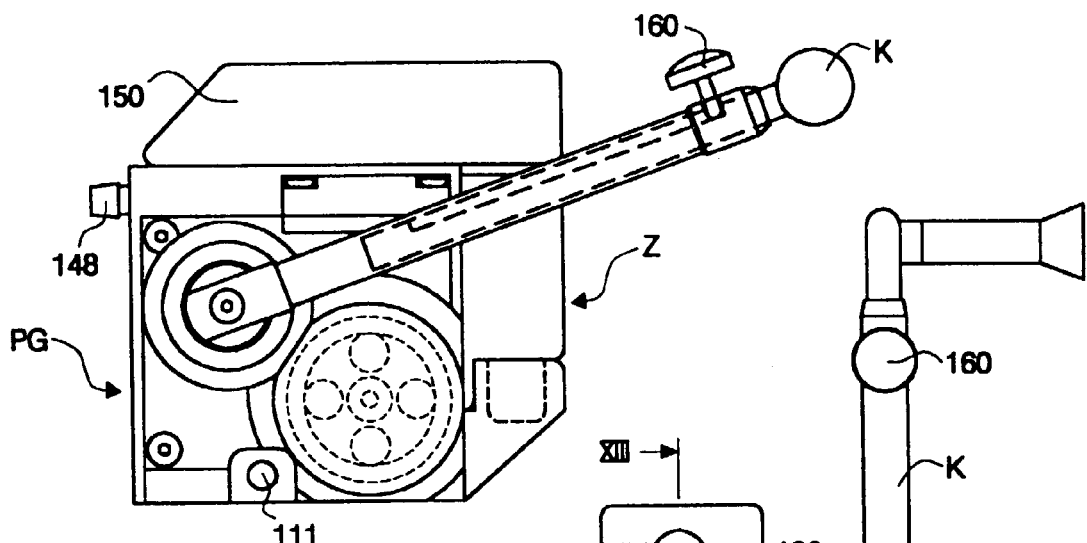
Figure 11:
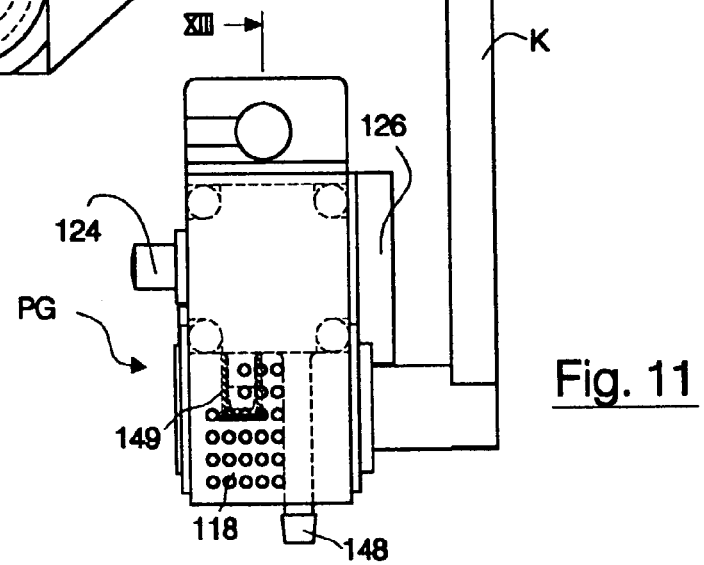
Figure 12:
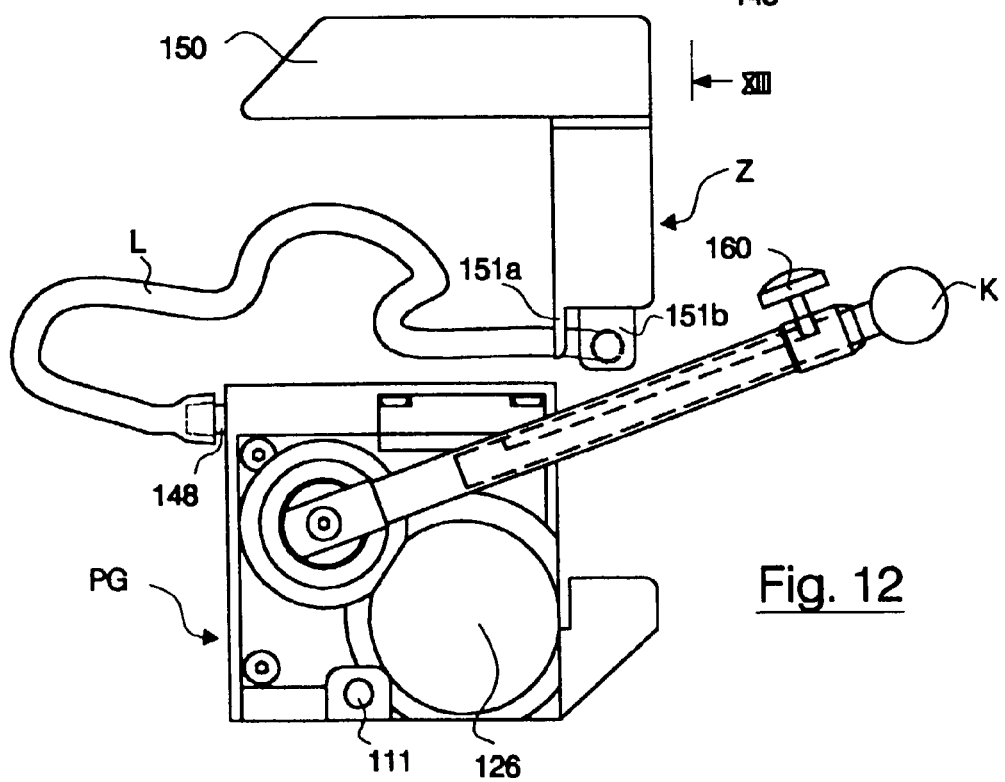
Figure 13:
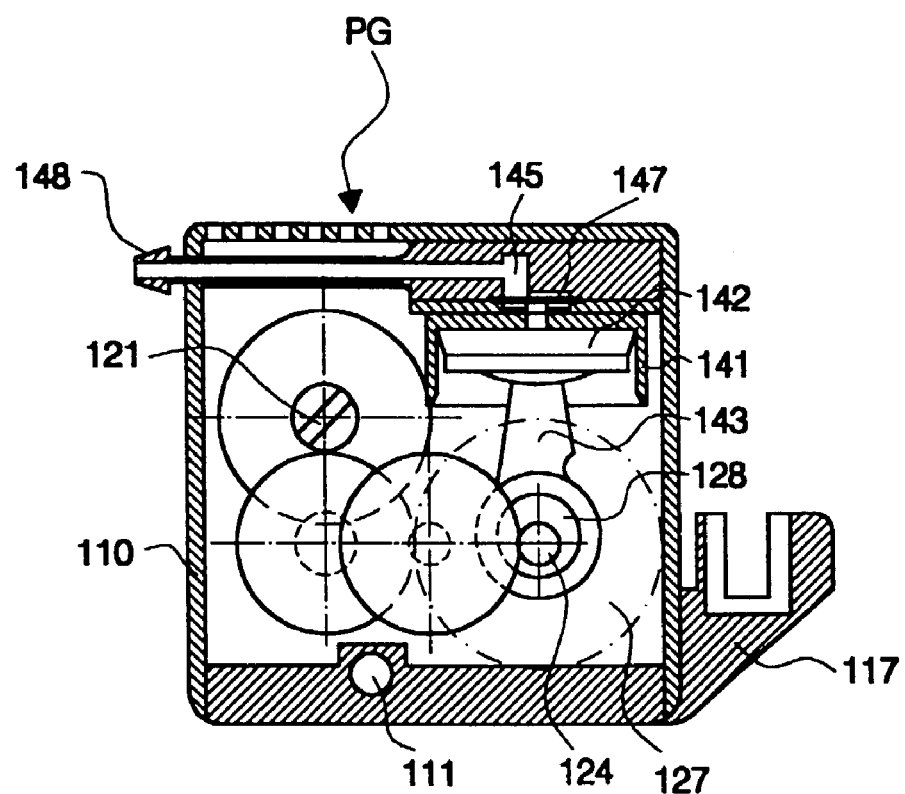
Figure 18:
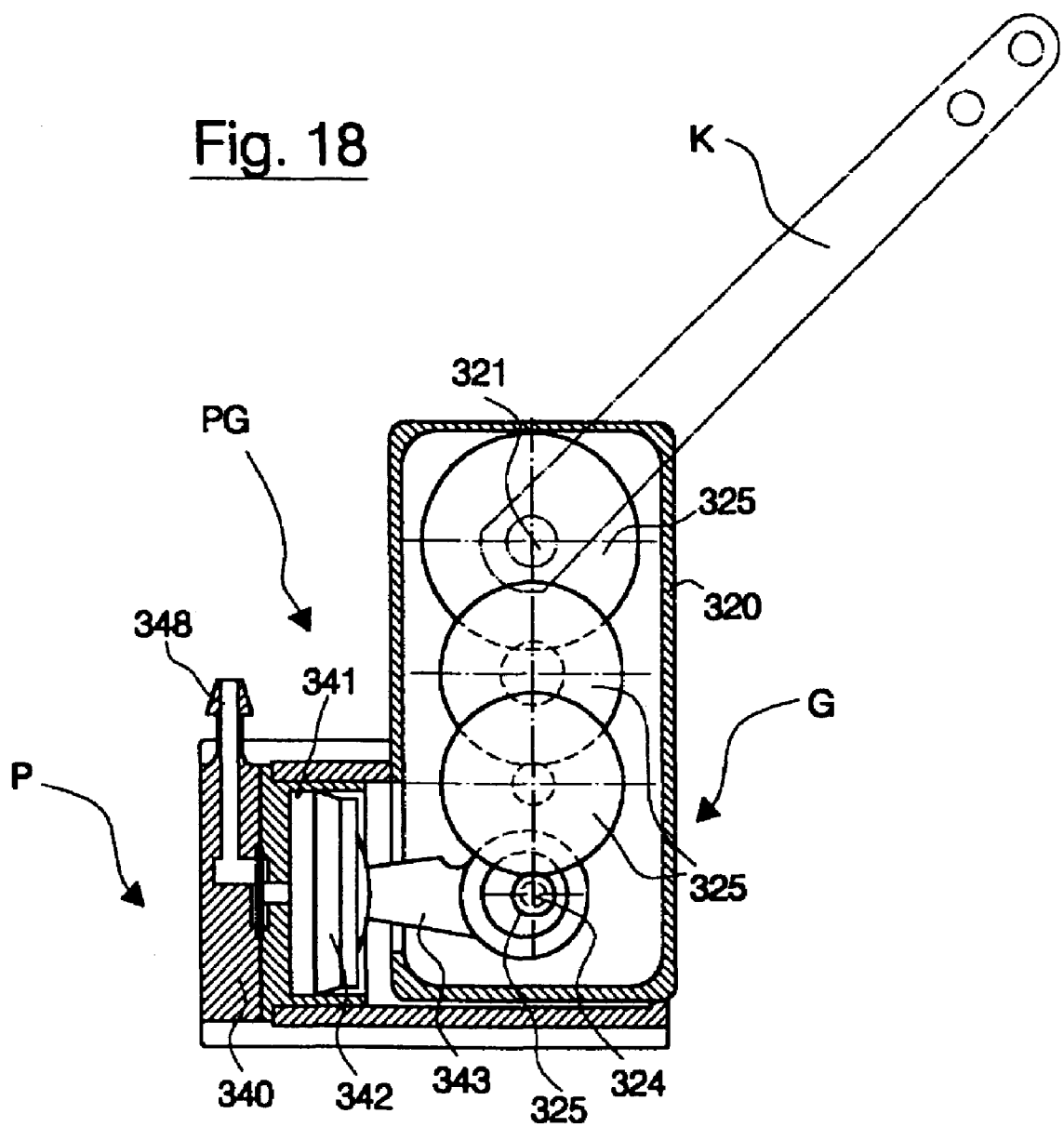
Figure 42:
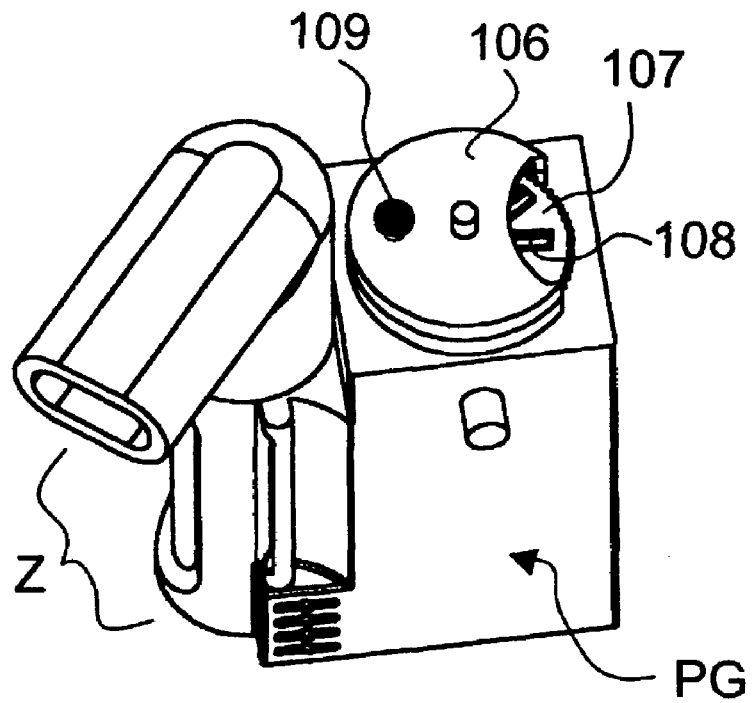
Figure 37:
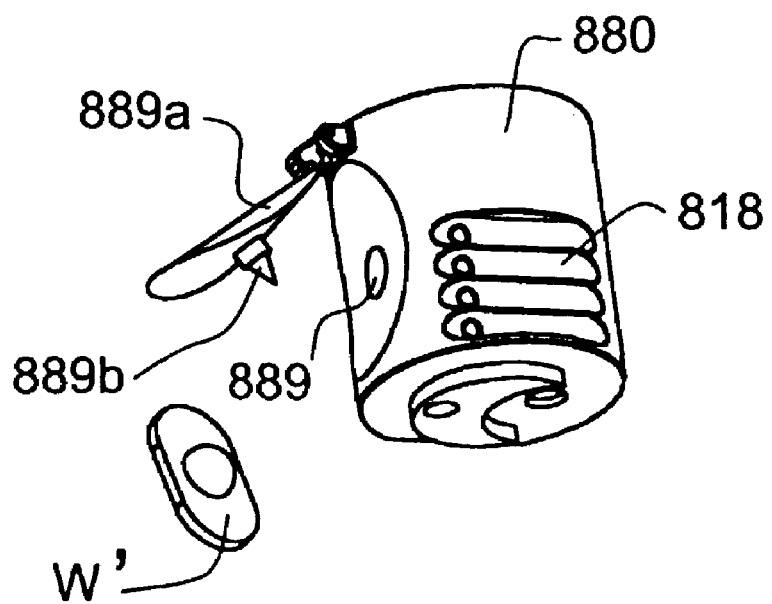
Figure 38:
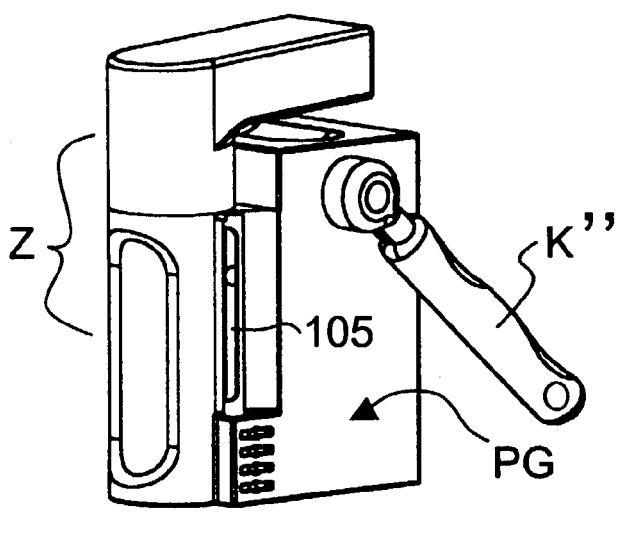
Figure 39:
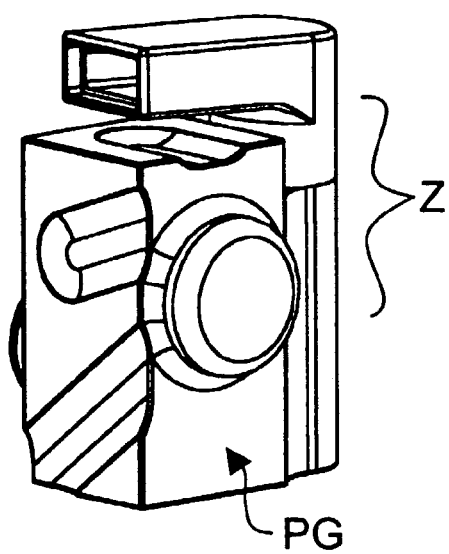
Figure 40:
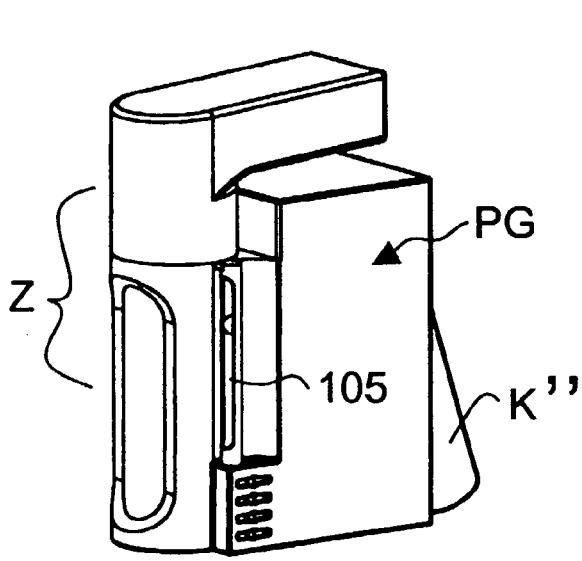
Figure 41:
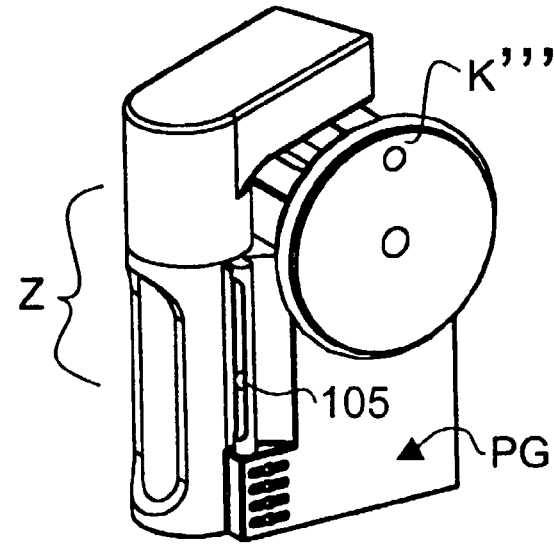

The following drawings illustrate exemplary embodiments of the invention in more detail. They show:

FIG. 1 shows a schematic drawing of an exemplary inhaler apparatus in which the nebuliser device of this invention can be used, FIG. 2 shows a longitudinal section through the pump and gear unit of a first concrete embodiment of the inventive inhaler apparatus, FIG. 3 shows a section along the line III—III of FIG. 2, FIG. 4 shows a section in analogy to FIG. 2, but in a representation rotated through 180°, through a variant of the pump and gear unit, FIGS. 5–8 show slightly simplified views of four embodiments of an inhaler apparatus equipped with a pump and gear unit in accordance with FIGS. 2 and 3, FIG. 9 shows a slightly simplified view of a further exemplary embodiment of an inhaler apparatus equipped with a pump and gear unit in accordance with FIG. 4, FIG. 10 shows a view of a further embodiment of an inhaler apparatus equipped with a modified pump and gear unit, FIG. 11 shows a view of the inhaler apparatus in the direction of the arrow XI in FIG. 10, but without nebuliser unit, FIG. 12 shows a view in analogy to FIG. 10, but with a nebuliser unit detached from the pump and gear unit, FIG. 13 shows a section along the line XIII—XIII of FIG. 11, FIG. 14 shows a section essentially analogous to FIG. 12 through the pump and gear unit of a further embodiment of an inhaler apparatus, FIG. 15 shows a section essentially along the line XV—XV of FIG. 14, FIGS. 16–17 show one view each of the pump and gear units of FIGS. 14 and 15 mounted on a stand, FIG. 18 shows a section analogous to FIG. 2 through an alternative exemplary embodiment of the pump and gear unit of the inhaler apparatus, FIGS. 19–21 show three partially sectioned views of a further embodiment of an inhaler apparatus equipped with a pump and gear unit in accordance with FIG. 18, FIGS. 22–24 show three views of a further exemplary embodiment of an inhaler apparatus equipped with a pump and gear unit in accordance with FIG. 18, FIG. 25 show a view of a further exemplary embodiment of an inhaler apparatus equipped with a pump and gear unit mounted on a stand in accordance with FIG. 18, FIG. 26 show a view of a further exemplary embodiment of an inhaler apparatus, built similarly to the one in FIG. 25 but additionally equipped with an electric drive, FIG. 27 show a view in the direction of the arrow XXVII of the embodiment of FIG. 26, FIG. 28 show a view in the direction of the arrow XXVIII of the lower part of the embodiment of FIG. 26, FIG. 29 show a longitudinal section along the line XXIX—XXIX of FIG. 30 through the inventive nebuliser device, FIG. 30 show a section along the line XXX—XXX of FIG. 29, FIG. 31 show a section along the line XXXI—XXXI of FIG. 29, FIG. 32 shows an oblique view of a further advantageous exemplary embodiment of an inhaler apparatus, FIG. 33 shows an exploded oblique view of the embodiment of FIG. 32, FIG. 34 shows an oblique view of a further advantageous exemplary embodiment of an inhaler apparatus, FIG. 35 show a section through an exemplary nebuliser device along the line XXXV—XXXV of FIG. 34, FIG. 36 show a section analogous to FIG. 35, but with a mixer housing rotated through 180°, FIG. 37 shows an oblique view of a detail variant of the embodiment according to FIG. 34, FIGS. 38–39 shows two oblique views of a further exemplary embodiment of an inhaler apparatus, and FIGS. 40–42 shows three further exemplary embodiments of an inhaler apparatus.

DETAILED DESCRIPTION OF THE PREFERRED EMBODIMENT

The most essential components of an example of the inventive inhaler apparatus and their functional interaction are best seen in the schematic general sketch of FIG. 1. Accordingly, the inhaler apparatus comprises a nebuliser unit or nebuliser device Z, a pump unit P and a gear unit G. In practice, the latter two are either lodged in a shared housing or are combined through other means to form a physical unit, henceforth called pump and gear unit PG.

The nebuliser device Z comprises a container chamber for a liquid active ingredient formulation as well as pneumatically driven nebulising means for the liquid active ingredient formulation. The compressed air required therefor is provided by the pump unit P, to the pressure side of which the nebuliser unit Z is connected by means of a preferably flexible tubing L. Alternatively, the tubing may also be foregone and the nebuliser unit Z can be connected to the pump unit P directly or by means of channels inside of the housing.

The pump unit P, which is built in the form of a crank gear, essentially comprises a short-stroke piston pump which works at relatively high stroke frequency and which is kinematically coupled to the gear shaft on the output side of the gear unit G and is driven by said gear unit.

The pump drive in the form of the gear unit G essentially comprises a gear transmission consisting essentially of toothed wheels equipped with one drive shaft, two intermediate shafts and one output shaft. A hand crank K is coupled to the drive shaft, preferably in detachable manner and, as mentioned earlier, the output shaft is kinematically connected directly to the piston of the short-stroke piston pump in the pump unit P which it drives oscillatingly. The transmission ratio is, for example, from about 1:10 to about 1:150, so that about 10 or about 150 revolutions of the output shaft correspond to one revolution of the hand crank. Correspondingly the stroke frequency of the piston pump is higher by the transmission ratio of the gear than the number of revolutions of the hand crank K.

Optionally, an electric motor M is provided which preferably can be coupled to the gear shaft on the output side through which it can drive the piston pump in the pump unit P. If the electric motor M is coupled, then the hand crank K is either taken off or is kinematically decoupled from the gear via suitable mechanical decoupling means so that it cannot co-rotate. Details in connection with this are discussed further below in connection with FIGS. 26–28.

The most important details essential to an exemplary embodiment of this invention regarding the mentioned main components of the inventive nebulising device and inhaler apparatus equipped with such nebulising device are discussed hereinbelow by means of FIGS. 2–42.

The embodiments of the inventive inhaler apparatus shown in FIGS. 2–9 all comprise the same build of the pump and gear unit PG, henceforth called “in-line configuration”, the construction of which is best seen in FIGS. 2 and 3.

The pump and gear unit PG comprises a shared and essentially parallel-epipedric housing 10 in which there are a gear housing 20 and a pump housing 40. The gear housing 20 and the parts which are in or on it together form the gear unit G, and the pump housing 40 and the parts which are in or on it together form the pump unit P.

One drive shaft 21, two intermediate shafts 22 and 23 and one output shaft 24 are mounted in rotatable manner in the gear housing 20 by means of unspecified bearings (or possibly also directly in the wall of the housing). One or two toothed wheels 25 each are wedged onto these four gear shafts 21–24, which toothed wheels mesh together and together form one gear transmission, the output shaft 24 rotating faster by the chosen transmission ratio than the drive shaft 21. The drive shaft 21 protrudes on one side or, preferably, on both sides (FIG. 4) from the housing 10, it being possible for the mentioned hand crank K to be attached in torque proof manner to the protruding shaft stump 21*a* and 21*b*. As the hand crank K can be attached to both sides, the inhaler apparatus is equally suitable for right-handers and left-handers alike.

In a covering box 26 fastened to the outside of the housing 10 a compensation wheel 27 is mounted in torque proof manner on the output shaft 24, which compensation wheel serves to avoid undesirable vibrations and has the corresponding dimensions. Additionally, an eccentric 28 sits in torque proof manner on the output shaft 24. The compensation wheel 27 may be provided with blades for the production of a secondary air stream which may be called upon for additional applications. The compensation wheel may furthermore also take the form of a toothed wheel and may serve for coupling the electric motor mentioned earlier on.

In the pump housing 40 there is a pump chamber 41 in which a pump piston 42 is arranged in a coaxially movable manner. The pump piston 42 is fixedly connected to a piston rod 43 which protrudes through unspecified apertures in the pump housing 40 and in the gear housing 20 into the latter and which kinematically meshes with the eccentric 28 such that at each revolution of the output shaft 24 the piston rod 43 and thus also the pump piston 42 moves back and forth once in the pump chamber (up and down in the drawing). The piston stroke is in this case given by the eccentricity of the eccentric 28.

The pump piston 42 is slightly elastic and is mounted in the pump chamber such that it has a little clearance so that the tipping motions produced by the eccentric 28 are irrelevant and a flexible build of the piston rod may be foregone.

One suction channel 44 and one discharge channel 45 each lead into the compression chamber of the pump chamber 41 positioned above the pump piston 42, in which two channels one diaphragm valve 46 and 47 each is arranged. The two diaphragm valves 46 and 47 are built in per se known manner such that, owing to the compression ratios in the compression chamber of the pump chamber 41, they open and close reciprocally so that air can only be lead into the pump chamber via the suction channel 44 and can only be lead away from the pump chamber via the discharge channel 45, a pumping effect being thus created. The suction channel 44 leads to a suction aperture opening into the environment, which suction aperture is not depicted but which is provided at the pump housing 40 and which is preferably equipped with an air filter. The discharge channel 45 communicates with a connecting nipple or connecting piece 48 located at the pump housing 40. Connected to this connecting nipple 48 is, at the latest when the inhaler apparatus is being used, the flexible tubing L mentioned earlier, through which the compressed air produced by the pump unit P is lead to the nebuliser unit Z.

The oscillating pump piston creates vibrations which can be very largely avoided by means of suitable dimensions of the compensation wheel. For this, the mass and thus the moment of inertia of the compensation wheel must be attuned to the piston stroke and to the nominal stroke frequency of the piston pump. The optimum attunement of the compensation wheel can be easily determined with a few practical tests.

A cylindrical drill hole 11 is provided in the lowest part of the housing 10, into which drill hole a clamping mandrel may be introduced in order to make it possible to fasten the pump and gear unit PG to a support, for example by means of a suitably shaped clamp iron.

The embodiment variant of FIG. 4 differs from that of the FIGS. 2 and 3 only in that the drive shaft 21 is provided on both sides with shaft stumps 21a and 21b which protrude from the housing 10 and which are used for fastening the hand crank K.

The FIGS. 5–8 illustrate the practical handling of the inhaler apparatus equipped with the pump and gear unit PG in accordance with FIGS. 2–3.

Figure 5:
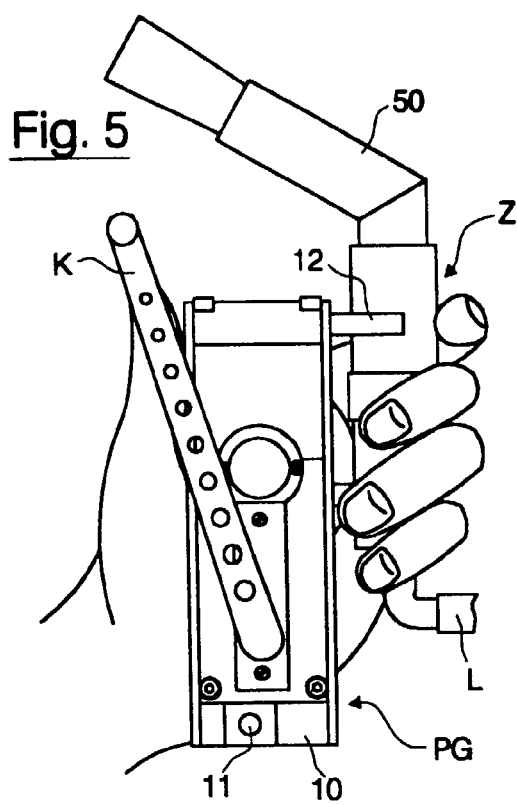

In the case of the embodiment of FIG. 5 the pump and gear unit PG is held directly in the hand, two holding forks 12 being provided at the housing 10 into which the nebuliser unit Z (described in more detail hereinbelow) can be locked in detachable manner. The nebuliser unit Z is provided here with an angled mountable mouth-piece 50.

Figure 6:
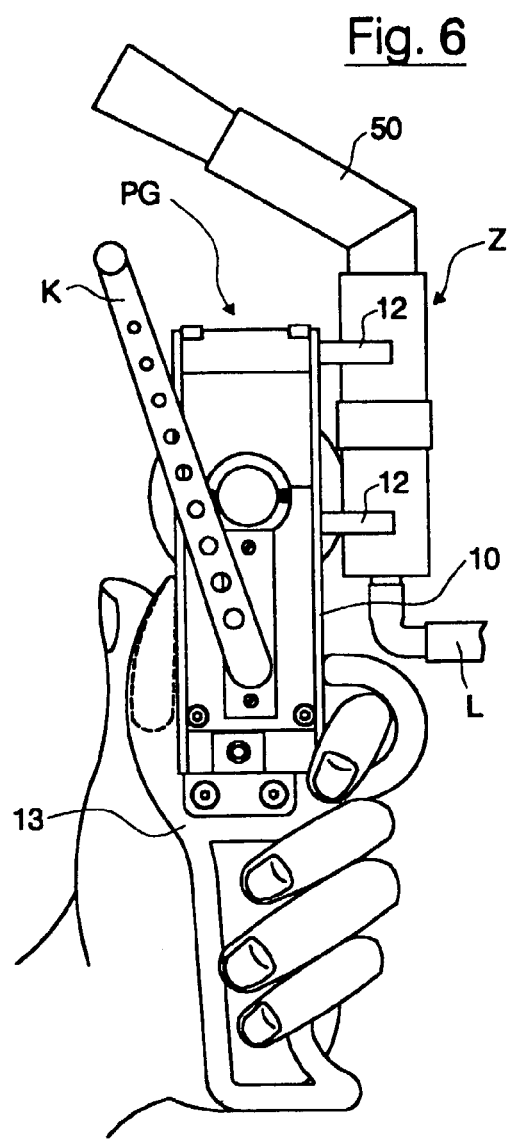

In the case of the embodiment of FIG. 6 a handle 13 attached to the housing 10 is additionally provided, by means of which handle the device can be comfortably held.

FIG. 7 illustrates how the pump and gear unit PG can be fastened to a support, e.g. to a table T, by means of a clamp iron 14. The clamp iron 14 is in this case equipped with a clamping mandrel 14a which meshes with the drill hole 11 in the housing 10.

In the embodiment of FIG. 8 the pump and gear unit PG or its housing 10 is provided with a flat hook-like organ (clip) 15 by means of which the unit PG can be hung or clipped onto e.g. a belt B. In a variant the pump-gear unit PG can in analogy to FIG. 4 also be arranged "upside down" at the belt B through which the tipping moments operative at the belt may be reduced.

FIG. 9 shows an embodiment in which the pump and gear unit PG is also arranged or held "upside down" as in FIG. 4. As in the embodiments of FIGS. 5–7, the nebuliser unit Z is attached to the housing 10 in detachable manner by means of holding forks or holding clamps (not shown here) and is connected to the pump unit by means of the tubing (not visible here either). The (in the drawing lower) end of the housing 10 on the side of the pump is here furthermore provided with a dovetail lead 16 by means of which the pump and gear unit PG can be attached to a correspondingly built stand. The upside down arrangement and the resultant top point of application of the hand crank K result here in a particularly small overall height.

FIGS. 10–13 show another embodiment of the inventive inhaler apparatus which essentially differs from the embodiments described above only in that the pump and gear unit PG has an even more compact build.

As may be seen in particular from FIG. 13, the gear and the piston pump are arranged within a shared housing 110; there are no separate housings for the gear unit and the pump unit. Apart from the more compact reciprocal arrangement, the gear and the piston pump are essentially built the same as in the previous embodiments. The corresponding functional elements are referred to by reference numbers 100 times greater so that the significance and function of those elements which are not explicitly mentioned become quite clear and their further discussion may thus be forgone.

The housing 110 is provided on the outside with a plug-in socket 117 which interacts with a counterpart plug-in socket 151a/151b on the nebuliser unit Z so that the nebuliser unit Z can be fastened detachably to the housing 110, as may be seen in FIG. 10. The connection between the nebuliser unit Z and the discharge nipple 148 of the piston pump is in turn created through an elastic tubing L.

FIG. 11 furthermore also shows a suction port 149 provided with a filter through which the piston pump sucks in air. The connection to the environment is created through apertures 118 arranged in the housing 110.

In the case of this embodiment, the hand crank K is telescopic and can be arrested at the desired extension by means of a locking screw 160. This allows the user of the inhaler apparatus to adjust the required expenditure of force to his personal needs. The hand crank K can, of course, also be built in extensible form in all the other embodiments of the inhaler apparatus.

FIGS. 14 and 15 show another embodiment of the inhaler apparatus. Here the pump and gear unit PG is built in analogy to the one of the embodiment of FIGS. 10–13, but the toothed wheels 225 of the gear are intended for a higher transmission ratio and the compensation wheel 227 is located at the side of the housing 210 facing the hand crank K. Analogous functional elements in this embodiment are referred to by reference numbers 100 or 200 times greater than those of the prior embodiments so that the significance and the function of those elements which are not explicitly mentioned become quite clear and their further discussions may thus be foregone.

FIGS. 16 and 17 show how the inhaler apparatus of the FIGS. 14 and 15 can be used stationarily. For this the pump and gear unit PG is installed on a stand 270 which in turn is mounted detachably, e.g. by means of a dovetail lead 271, onto a suction base 272 which is known per se. By means of the suction base 272 the entire apparatus can be detachably fastened to an even support having a sufficiently smooth surface. The pump and gear unit PG may be mounted onto the stand 270, for example in analogy to FIG. 7, by means of a tension mandrel 273 which meshes with a corresponding aperture (not depicted) in the housing 210.

FIG. 18 provides a sectional view of a variant of the pump and gear unit PG. In this variant, similarly to the embodiment of FIGS. 2 and 3, a gear unit G and a pump unit P are provided in housings 320 and 340 of their own, but these two units are not arranged in linear fashion one after the other but are configured in the form of an "L", i.e. the pump unit P is attached to the side of the gear unit G. The connection nipple 348 protruding from the pump housing 340 is arranged parallel to the longitudinal extension of the gear housing 320. Apart from this, all functional elements of the pump and gear unit PG of this embodiment are built the same as the corresponding elements of the previous embodiments. They are referred to by reference numbers 300 times greater than those of the embodiment of FIGS. 2 and 3 so that the significance and function of those elements which are not explicitly mentioned become quite clear and their further discussion may be foregone. By means of the L-shaped reciprocal arrangement it is possible to achieve an ergonomically advantageous outer shape as is evident from FIG. 19.

The inhaler apparatus of FIGS. 19–21 is provided with a holding strap 375 through which the user reaches to thus hold the apparatus more comfortably. Furthermore, in this embodiment the nebuliser unit Z is not connected to the pump unit by means of a tubing but is mounted by means of a slightly elastic adapter piece 352 onto the discharge nipple 348 of the pump unit P. The special build of the nebuliser unit Z shall be discussed hereinbelow. The elastic build of the adapter piece 352 slightly attenuates the unavoidable deflection of the device when the crank K is being rotated so that the user can hold the mouthpiece (not shown) of the nebuliser more comfortably in his mouth. The FIGS. 19–21 furthermore show an inlet nipple 349, provided with an air filter slipped over it, for the supply of air to the piston pump. If the device is used stationarily, for example in analogy to FIG. 7 or 16, then the nebuliser unit Z can of course be taken off and be connected to the pump unit P via a tubing.

FIGS. 22–24 show a further variant of the inhaler apparatus which differs from the embodiment of FIGS. 19–21 mainly through an alignment of the gear unit G with the direction of the use position and through a handle 413. The relative arrangement of pump unit P and gear unit G is the same as in FIG. 18. Additionally, the gear unit G is provided with a mount 452 into which the nebuliser unit Z can be tightly fitted. The mount 452 has an air channel 452a, one side of which opens into the container chamber 452b for the nebuliser unit Z and the other side of which is connected via a short tubing L to the discharge nipple 448 of the pump unit P. This embodiment of the inventive inhaler apparatus is distinguished by being especially compact.

FIG. 25 shows another embodiment of the inhaler apparatus in stationary use. In this case a pump and gear unit PG in accordance with FIGS. 18–21 is detachably fixed to a suction base 572 by means of an adapter 513 which is attached to the unit and which can also serve as a handle. The suction base 572 has two vertical bolts 572a and 572b on which the adapter 513 is mounted, which bolts mesh with two drill holes 513a and 513b provided in the adapter. When the inhaler apparatus is to be held by hand the adapter needs only to be stripped from the suction base, upon which the device can be held by the adapter serving as a handle.

Tests have shown that the gear unit can be produced as a very small unit which operates almost noiselessly.

FIGS. 26–28 show another embodiment of the inhaler apparatus. It comprises a pump and gear unit PG in the same configuration as the one depicted in FIGS. 18–21. The pump and gear unit PG is detachably mounted resting on an adapter 613 built in principle the same as the one according to FIG. 25. In analogy to FIG. 25 the adapter 613 is mounted on two bolts 672a and 672b provided at a suction base. The nebuliser unit connected to the pump unit via a tubing is not shown in the drawings.

In the adapter 613, which likewise also serves as a handle, there is an electric motor M which can be supplied with electric energy via a connecting cable $M_1$. The gear unit G is positioned on the adapter such that the shaft $M_2$ of the electric motor M is in exactly coaxial position to the output shaft 624 of the gear unit G. Interacting coupling elements 624a and 624b are fixed in torque proof manner on the output shaft 624 and on the motor shaft $M_2$, which coupling elements kinematically connect the electric motor M with the output shaft 624 of the gear unit G so that the electric motor drives the output shaft.

When the pump and gear unit PG is mounted on the adapter 613, i.e. normally in stationary use using the suction base 672, the piston pump is driven by the electric motor M. In this case the hand crank is not required and is therefore taken off from the shaft stump 621a of the drive shaft of the gear unit G. The protruding shaft stump 621a is then preferably protected by a collar 621 provided on the housing of the gear unit G.

To switch to the manual drive, the pump and gear unit PG is taken off from the adapter 613. Alternatively it is also possible to break the coupling between the electric motor M and the gear in suitable manner. And finally, it is also possible to leave the electric motor M coupled since it does not provide any substantial resistance to the rotary movement. For the manual use the pump and gear unit PG may also be left on the adapter 613 which may then serve as a handle.

The following Table shows some measurement examples for the piston pump and the gear unit as well as the output rate and overpressures achieved at e.g. nominal rotational speeds of the hand crank.

| piston Ø [mm] | piston stroke [mm] | gear transmission | number of revolutions [r per min] | vol. -current [ml/min] | overpressure [kPa] |
| --- | --- | --- | --- | --- | --- |
| 24 | 2.5 | 1:100 | 56 | 6330 | 110 |
| 24 | 3.5 | 1:100 | 48 | 7596 | 250 |
| 24 | 1.7 | 1:100 | 68 | 5227 | 70 |
| 24 | 2.0 | 1:150 | 56 | 7596 | 130 |
| 24 | 3.5 | 1:39 | 60 | 3700 | 130 |

The piston pump and the gear transmission G, which are in the pump unit P, are together designed such that the piston pump produces an air stream having an overpressure in the range of about 50–300 kPa (0.5–3 bar) at an output rate of about 1000–10000 ml/min, a number of revolutions of the manually driven hand crank being used as a base which is reasonably producible in most practical circumstances (at a magnitude of 1 revolution per second). The air stream thus produced is lead to the nebuliser unit Z. The build of the nebuliser unit is of utmost importance for a sufficiently fine nebulisation of the liquid active ingredient formulation stored in the nebuliser unit and for a uniform charging of the air stream emerging through the mouthpiece of the nebuliser unit.

The construction of a particularly useful embodiment of the inventive nebuliser device or nebuliser unit Z shall now be described in more detail by means of FIGS. 29–31.

The nebuliser unit comprises a nebuliser housing 80 and a mixer housing 90 which is coaxially, and preferably detachably, fixed thereon. The nebuliser unit 80 is essentially cup-shaped and forms a container chamber for the liquid active ingredient formulation W to be nebulised. At the (in the depicted normal use position) lower end or bottom of the nebuliser housing 80 an air inlet 81 is provided onto which the tubing L is, or may be, mounted to provide the connection to the pump unit. The air inlet 81 continues inwards in an essentially conical nozzle 82 which protrudes over the nominal maximum level of the active ingredient formulation W in the nebuliser housing 80, opening into a slit 83 which is provided in a crossbar 84 of a nebuliser body, referred to by 85 as a whole, and penetrating this crossbar. The nebuliser body 85 comprises essentially the crossbar 84 mentioned above and a cone 86 which is counterpart to the nozzle 82 and which sits with perfect fit on the nozzle 82. In the inner wall of the cone 86, two grooves 87 are arranged in diametric opposition along jacket lines of the cone and extend over its entire jacket length, which grooves, together with the outer wall of the nozzle 82, form two suction channels for the liquid active ingredient formulation. Alternatively, the two grooves can also be arranged in the outer wall of the conical nozzle 82. It is furthermore also possible that several grooves are provided. When the mixer housing 90 is taken off from the nebuliser housing 80, the liquid active ingredient formulation W can be directly filled into the nebuliser housing 80 or else also through it via the passages 88 remaining at both sides of the crossbar 84 between the latter and the inner wall of the nebuliser housing. Another possibility is the supply through a feed opening at the side of the nebuliser housing (compare FIGS. 33–37).

The essentially entirely cylindrical mixer housing 90, which is coaxially inserted into the nebuliser housing 80, comprises (in the illustrated embodiment four) axially parallel mixing channels extending through the entire mixer housing in the form of cylindrical drill holes 91–94 comprising one mixing body 95 each. At its (in the depicted use position) upper end the mixer housing 90 has a collar 96 in which a mouthpiece 50 of suitable build (having a small air inlet opening at its back) is mounted during use. The preferably plastic mixing bodies 95 consist of e.g. four axially meshing consecutive mixing elements 97 which in turn essentially consist of helicoids rotating in opposite directions. The adjacent mixing elements 97 are in this case preferably rotationally staggered through 90°. The drill holes 91–94 form together with the mixing channels 95 in them four continuous ducts, the special build of the mixing bodies 95 and their mixing elements 97 effecting a frequent change of the flow direction and thus a thorough and turbulent mixing of the air flowing through the ducts. Of course it is also possible that more or fewer mixing bodies 95 are provided. The mixing body or bodies 95 may, for example, also be provided with an antimicrobial coating.

During the use of the inhaler apparatus or of the nebuliser device Z an air stream under a relatively slight overpressure in the range from about 50 to about 300 kPa is lead from the pump unit Z e.g. via the tubing L into the nebuliser unit Z. The air supplied emerges through the tip of the nozzle 82 and through the slit 83 into the free space at both sides of the crossbar 84. Owing to the Venturi effect a suction effect is created in the area of the discharge apertures of the two suction channels 87 due to which liquid active ingredient formulation W is sucked in the form of finest liquid particles and is carried along by the emerging air stream. Possible coarser liquid particles flow back into the container chamber of the nebuliser chamber.

The air charged with the liquid particles is first laterally diverted directly above the nozzle tip by the crossbar 84 which acts as an impact element and then flows through the (in this case four) drill holes 91–94 containing the mixing bodies 95, finally leaving the nebuliser unit Z through the mounted mouthpiece 50. The impact surfaces or flow baffles created by the mixing bodies 95 and their mixing elements 97 effect a shattering of the particles and hence a further diminution of the liquid particles as well as a thorough mixing and uniform distribution in the air stream charged therewith. Tests have shown that despite this comparatively simple and "rough" construction it is possible to obtain in this manner a virtually 100% proportion of liquid particles having a size of max. 5μ. This extremely advantageous result is obtained within wide limits relatively independently from the overpressure of the supplied air stream, which is important in particular in connection with the manual drive of the pump unit since the actual pressure in manual use is subject to relatively large fluctuations owing to various influencing factors. The nebuliser device is (under normal use conditions) "rupture proof", i.e. in the normal use position and at the overpressures normally obtained in practice through manual drive the air stream cannot be deleteriously overcharged with active ingredient formulation and it is even less likely that non-nebulised liquid active ingredient formulation is exhausted into the respiratory tract.

Because of the relatively small passage apertures in the area of the tip of the nebuliser body 85a relatively high resistance to fluid flow is created which, so to speak, hydraulically decouples the nebuliser system from the flow conditions in the mouthpiece.

FIGS. 32–36 show two additional embodiments of the inventive inhaler apparatus which are especially useful in particular because of their easy cleanability. Those elements corresponding to, or having the same function as in, the embodiments discussed so far are given reference numbers 700 or 800 times greater than those of the first embodiment so that a detailed discussion of these elements may be foregone.

The two embodiments have in common that they consist of three physical functional units which are detachably fitted together and which are held together by a tension clamp 700 and 800. The three functional units are formed on the one hand by the pump and gear unit PG and on the other hand by the nebuliser part and the mixer part of the nebuliser unit Z. The tension clamp 700 and 800 is in each case hinged to the pump and gear unit PG and in the embodiment of the FIGS. 32 and 33 meshes (in the closed state) with the mixer housing 790 or, in the embodiment of the FIGS. 34–36, with an annular groove at the mixer housing 890. By folding the tension clamp 700 and 800 back, the meshing is released and the three functional units can be taken apart.

The exploded drawing of FIG. 33 shows particularly clearly how the inhaler apparatus is constructed and assembled. Together with the gear G and the compensation wheel 727 the pump P is pre-assembled and inserted as a whole into the housing of the pump and gear unit PG. It is possible to see the connecting nipple 748 and the suction channel 744 of the pump P at the pump and gear unit PG which is open on top.

The nebuliser part and the mixer part of the nebuliser unit Z are essentially built the same as in the embodiment of the FIGS. 29–31 which is also evident from the sectional views of the FIGS. 35 and 36. A difference essentially only consists in that the mixer housing 790 and 890 only has one single mixing channel 891 (FIG. 35) and accordingly also only one mixing body 795 and 895, and in that the mouthpiece 750 and 850 (provided with a small aperture in its back) is moulded directly on the mixer housing 790 and 890.

The nebuliser body 785 and 885 is removably inserted into the nebuliser housing 780 and 880. The mixing body 795 and 895 is likewise removably inserted into the mixer housing 790 and 890. This warrants on the one hand that the inhaler apparatus may be easily produced and on the other hand that the individual elements can easily be cleaned if necessary.

The nebuliser housing 780 and 880 and the pump and gear unit PG are mechanically coordinated in such a way that a close connection is produced in the assembled state, with the connecting nipple 748 and 848 leading directly into the nebuliser body 785 and 885 and, on the other hand, with the suction channel 744 and 844 communicating with air inlet slits 718 and 818 located at the side of the nebuliser housing 780 and 880.

In order to prevent the active ingredient formulation in the nebuliser housing from leaking out, the nebuliser housing 780 of the embodiment of FIGS. 32 and 33 is provided with a slide 788 with which the nebuliser housing 780 can be closed. Alternatively, in the case of the embodiment of FIGS. 34–36 the mixer housing 890 is arranged rotatably on the nebuliser housing 880, the mixing channel 891 in the one rotated position (FIG. 35) communicating with the interior of the nebuliser housing 880 and in the other rotated position, rotated through 180° (FIG. 36), the nebuliser housing 880 being closed by the mixer housing 890.

It is possible to fill in the active ingredient formulation while the mixer housing is removed. However, a feed opening 789 and 889 is preferably provided at the side of the nebuliser housing 780 and 880, which opening is connected to the interior of the nebuliser housing (FIG. 33, FIG. 37). In accordance with the detail variant of FIG. 37, the feed opening 889 can also be built for receiving a single dose blister pack W' of the active ingredient formulation. A lid 889*a* with a mandrel 889*b* hinged at the nebuliser housing 880 in this case closes the feed opening 889 and can at the same time be used for pricking open the blister pack.

The embodiment depicted in the FIGS. 38 and 39 follows that of FIG. 24, the mouthpiece, however, being built similarly to the one in FIGS. 32–36 in one piece with the mixer housing. To make the handling easier and safer, handle depressions, not specified in detail, are incorporated in the pump and gear unit PG and in the nebuliser unit Z. By means of coupling and springing means (not depicted) the hand crank K' is furthermore coupled with the gear in such a way that it does not necessarily have to be rotated fully but that through repeated pushing (swivelling in the direction of the pump and gear unit PG) and letting go (spring-driven swivelling back) the toothed wheels of the gear are made to rotate in the same direction (principle of a ratchet). Because of this it is possible to operate the inhaler apparatus with only one hand. Of course the hand crank K may also be cranked continuously as in the other embodiments.

In addition, a flow indicator 105 is provided to check the air stream produced by the pump. Said flow indicator consists in a manner know per se of a (in use position about) vertical transparent duct section which is connected to the pressure or suction side of the pump and which contains a small ball which, depending on the flow speed, rises higher or less high in the duct section passed through by the air stream. The embodiments of FIGS. 40–42 are also equipped with such a flow indicator. The flow indicator permits the user to check whether he is cranking sufficiently.

In the case of the embodiment of FIG. 40 the hand crank K″ is not hinged to the side of but to the inside of the housing of the pump and gear unit PG. In the embodiment of FIG. 41 the hand crank is replaced by a hand wheel K′″ which, similarly to the hand crank K', can be swivelled back and forth using thumb and index finger, but which can also be rotated continuously like a normal crank.

The embodiment according to FIG. 42 is similar to the one according to FIG. 38. The mixer housing of the nebuliser housing Z with the integrated mouthpiece is slightly swivelled so that the upper side of the housing of the pump and gear unit PG is free. On the latter an about cylindrical container chamber 106 is arranged in which there is a rotatable blister disk 107 containing a series of single dose blisters 108 of the active ingredient formulation. A mandrel 109, which can be actuated from the outside, serves for pricking open one of the single dose blisters lying underneath, upon which the liquid active ingredient formulation therein flows through channels (not depicted) into the interior of the nebuliser housing Z.

The inhaler apparatus warrants not only a good particle distribution and hence an optimum effect at shortest inhalation time but is also especially small and handy and is thus ideally suitable for mobile use. Because of its modular build it can be used in various ways (hand apparatus, stationary apparatus) and moreover also requires only a very small package and transport volume. The manual drive eliminates the need for any other energy supply as well as the maintenance expenditure normally associated therewith. The inhaler apparatus is not susceptible to trouble and can be used any time and anywhere immediately and without any preparatory manipulations and is therefore ideal for mobile and emergency use.

The active ingredient formulation is already brought to the correct particle size within the inhaler apparatus so that the device is largely independent of the force and speed of the breath. No forced breath manoeuvres are required and holding the breath at the end of the inhalation has no effect worth mentioning on the deposition of the active ingredient particles. The active ingredient formulation can comprise a vehicle substance in a manner known per se. The inhaler apparatus is also suitable for nasal applications and does not require any propellant gas.

It will be appreciated by those skilled in the art that the present invention can be embodied in other specific forms without departing from the spirit or essential characteristics thereof. The presently disclosed embodiments are therefore considered in all respects to be illustrative and not restricted. The scope of the invention is indicated by the appended claims rather than the foregoing description and all changes that come within the meaning and range and equivalence thereof are intended to be embraced therein.

What is claimed is:

1. An inhaler apparatus for producing and releasing an air stream charged in controlled manner with fine liquid active ingredient particles, said apparatus comprising:

a pump unit (P) for producing a stream of compressed air, a hand-operated drive (G) for the pump unit and a pneumatically driven nebuliser device (Z) communicating with the pump and having a container chamber (80) for holding a liquid active ingredient formulation (W), said pump unit comprising a short-stroke piston pump (41–43) having an air outlet and a pump piston (42), the stroke of which is not substantially more than three millimeters, said drive being built in the form of a crank gear (G) comprising a gear transmission (21–25) and a hand crank (K) for driving said gear transmission, said gear transmission having an output shaft (24) being kinematically connected to the pump piston (42) via and eccentric (28) thus driving said pump piston, said nebuliser device (Z) being equipped with a self-priming nebuliser nozzle (82) and with a connection (81) for leading compressed air into the nebuliser nozzle, wherein said connection (81) is connected to the outlet of said piston pump, said nebuliser device (Z) further comprising mixing means (90–97) in-line with the nebuliser nozzle (82) in the direction of the flow which repeatedly divert the air stream charged with liquid particles which emerges from the nebuliser nozzle (82), said mixing means comprising a plurality of longitudinally extended mixing channels (91–94) in which there is a mixing body (95) which provides baffles for the air stream charged with liquid particles which flows through the mixing channels, whereby said mixing body (95) comprises at least two mixing elements (97) in the form of helicoids rotating in opposite directions, and said nebuliser device being further provided with sealing means (788, 890, 891) to prevent liquid active ingredient formulation from leaking out of the nebuliser device.

2. An inhaler apparatus according to claim 1, wherein the mixing elements (97) are rotationally staggered.

3. An inhaler apparatus according to claim 1, wherein in-line with the mixing means 90–97) and in the direction of the flow there is a mouthpiece (850) communicating therewith which is provided with an additional air inlet.

4. An inhaler apparatus according to claim 3, wherein fluid resistance in an area of a tip of the nebuliser nozzle (82) is such that a fluidic uncoupling from flow conditions in the mouthpiece (850) is brought about.

5. An inhaler apparatus according to claim 1, wherein an impact element (84) provided immediately downstream of the nebuliser nozzle (82) which at least partly diverts the air stream immediately after its emergence from the nebuliser nozzle (82).

6. An inhaler apparatus according to claim 1, wherein a nebuliser body (85) is provided which encloses the nebuliser nozzle (82) and which forms together with said nozzle at least one suction channel (87) through which the liquid active ingredient formulation (W) can flow into an area of a discharge aperture in the nebuliser nozzle (82).

7. An inhaler apparatus according to claim 6, wherein the nebuliser body (85) is arranged loosely in the nebuliser device so that it can be removed without tools.

8. An inhaler apparatus according to claim 1, wherein the mixing body (95) is arranged loosely in the mixing channel 91–94 so that it can be removed without tools.

9. An inhaler apparatus according to claim 1, configured to receive at least one single-dose package (W') for the liquid active ingredient formulation (W) and being provided with at least one channel for connecting the single-dose package with the container chamber (80); and wherein means (889*b*, 109) are Divided to break the single-dose package (W'; 108) such that its contents empty through the channel into the container chamber (80).

10. An inhaler apparatus according to claim 1, wherein the mixing body (95) is provided with an antimicrobial effective coating.

11. An inhaler apparatus according to claim 1, wherein the piston pump (41–43) is provided with diaphragm valves (46, 47).

12. An inhaler apparatus according to claim 1, wherein the stroke of the piston pump is about 1.5–3.5 mm.

* * * * *